(12) United States Patent
Marasco et al.

(10) Patent No.: US 9,527,924 B2
(45) Date of Patent: Dec. 27, 2016

(54) HUMANIZED MONOCLONAL ANTIBODIES AND METHODS OF USE

(75) Inventors: Wayne A. Marasco, Wellesley, MA (US); Jianhua Sui, Stoneham, MA (US); Yuval Avnir, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 29 days.

(21) Appl. No.: 13/700,974

(22) PCT Filed: Jun. 2, 2011

(86) PCT No.: PCT/US2011/038970
§ 371 (c)(1),
(2), (4) Date: May 17, 2013

(87) PCT Pub. No.: WO2011/153380
PCT Pub. Date: Dec. 8, 2011

(65) Prior Publication Data
US 2013/0243749 A1 Sep. 19, 2013

Related U.S. Application Data

(60) Provisional application No. 61/350,790, filed on Jun. 2, 2010.

(51) Int. Cl.
| | | |
|---|---|---|
| *C07K 16/42* | (2006.01) | |
| *A61K 39/395* | (2006.01) | |
| *A61K 39/145* | (2006.01) | |
| *C07K 16/10* | (2006.01) | |
| *A61K 39/00* | (2006.01) | |
| *A61K 39/39* | (2006.01) | |

(52) U.S. Cl.
CPC ......... *C07K 16/4241* (2013.01); *A61K 39/145* (2013.01); *A61K 39/39566* (2013.01); *C07K 16/1018* (2013.01); *C07K 16/4216* (2013.01); *A61K 39/39* (2013.01); *A61K 2039/55516* (2013.01); *C07K 2317/24* (2013.01); *C07K 2317/56* (2013.01); *C07K 2317/567* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,051,359 B2 * | 6/2015 | Garcia-Sastre | ...... C07K 14/005 |
| 2006/0063209 A1 | 3/2006 | Meares et al. | |
| 2007/0081989 A1 * | 4/2007 | Sanders | ..................... 424/131.1 |
| 2009/0068637 A1 * | 3/2009 | Xia et al. | ......................... 435/5 |

FOREIGN PATENT DOCUMENTS

| | | |
|---|---|---|
| WO | WO 2007/035857 A2 | 3/2005 |
| WO | WO 2005/034733 A2 | 4/2005 |

OTHER PUBLICATIONS

Sui, et al. Structural and functional bases for broad-spectrum neutralization of avian and human influenza A viruses. Nature Structural and Molecular Biology. Feb. 22, 2009, vol. 16, pp. 265-273.

Mageed et al. "Immunogenic and Antigenic Epitopes of Immunoglobulins XVII. Monoclonal Antibodies Reactive with Common and Restricted Idiotopes to the Heavy Chain of Human Rheumatoid Factors" *Rheumatology International*. vol. 6, No. 4, 1986, pp. 179-184.

Widhopf et al. "Transgenic expression of a human polyreactive IG expressed in chronic lymphocytic leukemia generates memory-type B cells that respond to nonspecific immune activation" *Journal of Immunology*, Feb. 15, 2004, vol. 172, No. 4, pp. 2092-2099.

Potter et al. "Molecular characterization of the VH1-specific variable region determinants recognized by anti-idiotypic monoclonal antibodies G6 and G8" *Scandinavian Journal of Immunology*, vol. 50, No. 1, Jul. 1999, pp. 14-20.

Yazaki et al "Humanization of the anti-CEA T84.66 antibody based on crystal structure data" *Protein Engineering Design and Selection*, vol. 17, No. 5, Jan. 1, 2004, pp. 481-489.

Hohmann et al. "Mouse monoclonal anti-ideotypic antibodies to HIV p24: Immunochemical properties and internal imagery" *Molecular Immunology*, Pergamon, GB, vol. 30, No. 6, Apr. 1, 1993, pp. 521-527.

\* cited by examiner

*Primary Examiner* — Agnieszka Boesen
(74) *Attorney, Agent, or Firm* — Cooley LLP; Ivor Elrifi; Cynthia Kozakiewicz

(57) ABSTRACT

Disclosed is a humanized monoclonal antibody that binds to the human immunoglobulin heavy chain variable region germline gene VHI-69. The antibody is derived from Mab G6 and recognizes the same epitope. Moreover, the antibody is used in combination with vaccines to augment an immune response to the antigen.

4 Claims, 21 Drawing Sheets

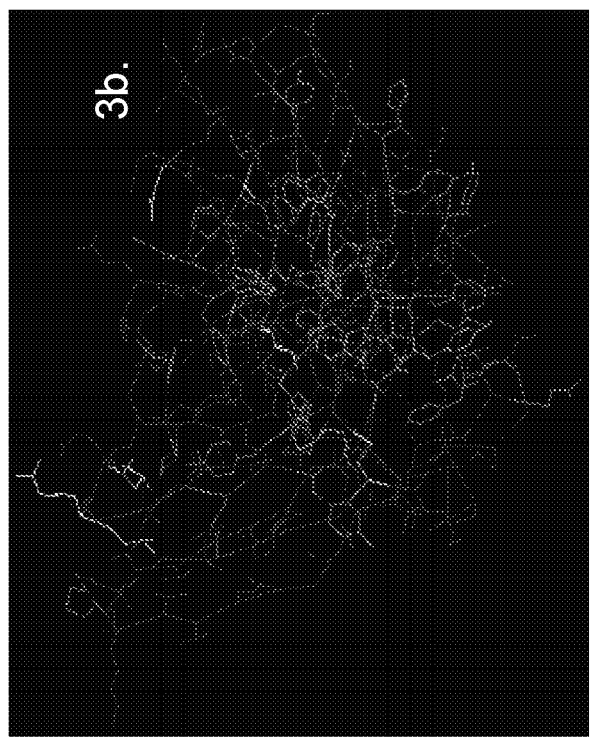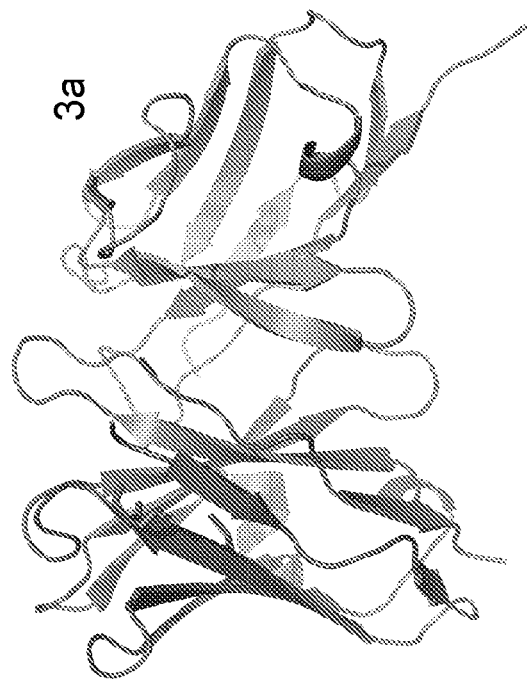
Fig. 3

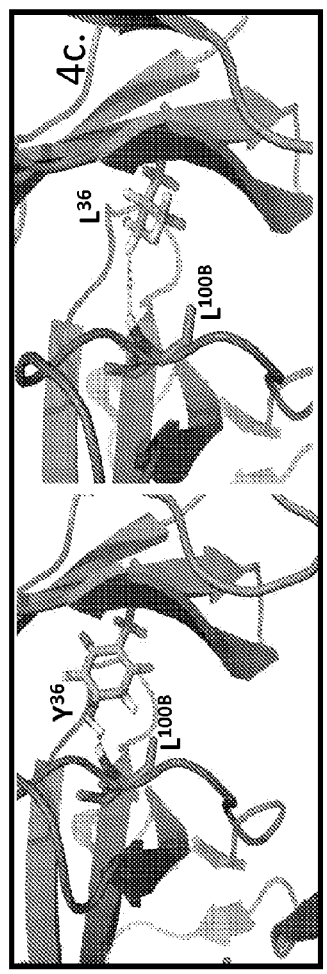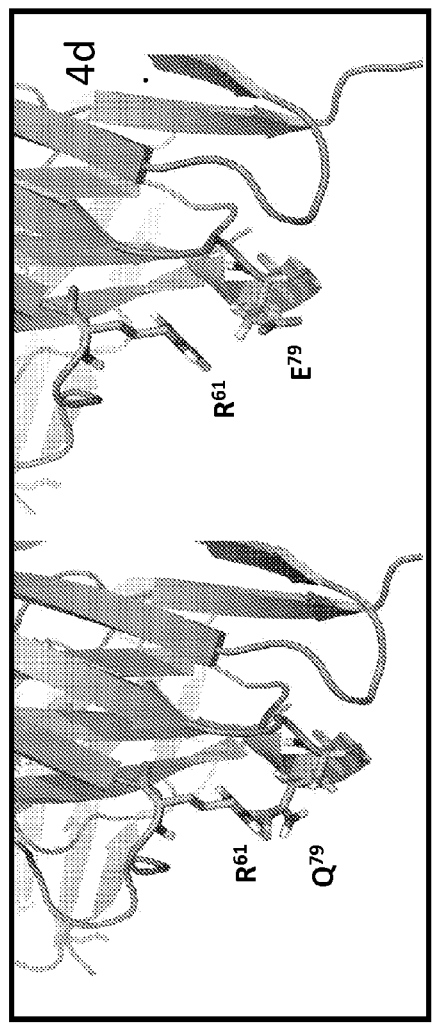
Fig. 4-continued

Fig. 13

| | FR1 | | | CDR1 | CDR2 | | | FR3 | | |
|---|---|---|---|---|---|---|---|---|---|---|
| | 2 | 6 | 17 | 33 | 50 | 54 | 56 | 71 | 73 | 85 |
| | V | Q | S | A | G | F | T | A | E | E |
| | GTG | CAG | TCG | GCT | GGG | TTT | ACA | GCG | GAA | GAG |
| 51p1-r | --C | --- | --- | A-- | A-- | C-- | -T- | --- | A-- | --- |
| | | | | T | R | L | I | T | K | D |
| hv1263-r | --- | --- | --- | --- | --- | --- | --- | --- | --- | -T- |
| Alleles | | | | | | | | | | |
| 1 | --C | --- | --- | --- | --- | --- | --- | --- | --- | --- |
| 2 | --C | --A | --- | A-- | A-- | C-- | -T- | --- | A-- | --- |
| 3 | --C | --- | --- | --- | --- | --- | --- | --- | A-- | --- |
| 4 | --C | --- | --- | --- | A-- | C-- | -T- | --- | A-- | --- |
| 5 | --C | --- | --- | --- | A-- | --- | --- | A-- | A-- | --- |
| 6 | --C | --A | --- | A-- | --- | --- | --- | --- | A-- | --- |
| 7 | --C | --- | --- | --- | A-- | C-- | -T- | --- | A-- | --- |
| 8 | --C | --- | --- | --- | A-- | C-- | -T- | --- | A-- | --- |
| 9 | --C | --- | --- | --- | A-- | C-- | -T- | --- | A-- | --- |
| 10 | --C | --- | --- | --- | --- | --- | --- | --- | --- | --- |
| 11 | --C | --- | --- | --- | --- | --- | --- | --- | --- | --- |
| 12 | --- | --- | --A | --- | --- | --- | --- | --- | --- | --- |
| 13 | --- | --- | --A | --- | --- | --- | --- | --- | --- | --- |

Fig. 16 (SEQ ID NO: 22)

SEQUENCE LISTING

<160> NUMBER OF SEQ ID NOS: 29

<210> SEQ ID NO 1
<211> LENGTH: 354
<212> TYPE: DNA
<213> ORGANISM: Homo sapiens

<400> SEQUENCE: 1
caggtccagc tcgtccagtc cggcgctgaa gtggtgaaac ccggggcatc cgtcaaagtc      60
tcttgtaagg ctagtggcta caccttcaca tcctactgga tgcattgggt gaaacaggca     120
cctggccagg gactcgaatg gatcggagcc gtgtctcctg gaaattccga cacctcctac     180
aacgaaaaat tcaagggcaa ggcaaccctc actgtggata ctagtgcttc taccgcctac     240
atggaactct catctctccg ctctgaggac actgccgtct actactgtac tcggtcacga     300
tacgggaaca acgctctcga ttactgggga cagggcacac tggtcactgt ctct            354

<210> SEQ ID NO 2
<211> LENGTH: 118
<212> TYPE: PRT
<213> ORGANISM: Homo sapiens

<400> SEQUENCE: 2

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Ser Tyr Asn Glu Lys Phe
    50                  55                  60

Lys Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Leu Val Thr Val Ser
        115

<210> SEQ ID NO 3
<211> LENGTH: 321
<212> TYPE: DNA
<213> ORGANISM: Homo sapiens

<400> SEQUENCE: 3
gatattcagc tcacacagag cccatcttct ctgtctgctt ctgtgggcga tcgagtgaca      60
atcacttgtc gggctagtca gggcatttct agcaacattg tgtggctcca gcagaaacct     120
ggcaaagccc caaaaggcct catctaccac ggaaccaacc tggaatctgg cgtgccatct     180
cggtttagtg gatctggatc cgggaccgat tacacactca ccatctcttc actggaacct     240
gaggatttcg ccacctacta ctgtgtccag tactcccagt ttccacccac ttttggacag     300
ggaaccaaac tcgagatcaa a                                                321

<210> SEQ ID NO 4
<211> LENGTH: 107
<212> TYPE: PRT
<213> ORGANISM: Homo sapiens

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asn
            20                  25                  30

Ile Val Trp Leu Gln Gln Lys Pro Gly Lys Ala Pro Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Thr Tyr Tyr Cys Val Gln Tyr Ser Gln Phe Pro Pro
                85                  90                  95

Thr Phe Gly Gln Gly Thr Lys Leu Glu Ile Lys
            100                 105

<210> SEQ ID NO 5
<211> LENGTH: 8
<212> TYPE: PRT
<213> ORGANISM: Homo sapiens

<400> SEQUENCE: 5

Gly Tyr Thr Phe Thr Ser Tyr Trp
1               5

<210> SEQ ID NO 6
<211> LENGTH: 8
<212> TYPE: PRT
<213> ORGANISM: Homo sapiens

<400> SEQUENCE: 6

Val Ser Pro Gly Asn Ser Asp Thr
1               5

<210> SEQ ID NO 7
<211> LENGTH: 12
<212> TYPE: PRT
<213> ORGANISM: Homo sapiens

<400> SEQUENCE: 7

Thr Arg Ser Arg Tyr Gly Asn Asn Ala Leu Asp Tyr
1               5                   10

<210> SEQ ID NO 8
<211> LENGTH: 9
<212> TYPE: PRT
<213> ORGANISM: Homo sapiens

<400> SEQUENCE: 8

Gln Gly Ile Ser Ser Asn Ile Val Trp
1               5

<210> SEQ ID NO 9
<211> LENGTH: 3
<212> TYPE: PRT
<213> ORGANISM: Homo sapiens

<400> SEQUENCE: 9

His Gly Thr
1

<210> SEQ ID NO 10
<211> LENGTH: 9
<212> TYPE: PRT
<213> ORGANISM: Homo sapiens

<400> SEQUENCE: 10

Val Gln Tyr Ser Gln Phe Pro Pro Thr
1               5

<210> SEQ ID NO 11
<211> LENGTH: 354
<212> TYPE: DNA
<213> ORGANISM: Homo sapiens

<400> SEQUENCE: 11
caggtccagc tcgtccagtc cggcgctgaa gtggtgaaac ccggggcatc cgtcaaagtc      60
tcttgtaagg ctagtggcta caccttcaca tcctactgga tgcattgggt gaaacaggca     120
cctggccagg gactcgaatg gatcggagcc gtgtctcctg gaaattccga cacctcctac     180
aacgaaaaat tcaagggcaa ggcaaccctc actgtggaca atctgcctc taccgcctac     240 atggaactct catctctccg ctctgaggat actgctgtgt actactgtac ccggtcacga     300
tacggcaata acgccctcga ttactggggg cagggaactc tggtcactgt gtct           354

<210> SEQ ID NO 12
<211> LENGTH: 118
<212> TYPE: PRT
<213> ORGANISM: Homo sapiens

<400> SEQUENCE: 12

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Ser Tyr Asn Glu Lys Phe
    50                  55                  60

Lys Gly Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Leu Val Thr Val Ser
        115

<210> SEQ ID NO 13
<211> LENGTH: 357
<212> TYPE: DNA
<213> ORGANISM: Mus musculus

<400> SEQUENCE: 13
caggtccagc tgcagcagtc tgggactgtg ctcgcaaggc ctggggcttc agtgaagatg      60
tcctgcaagg cttctggcta cacctttacc agttactgga tgcactgggt aaaacagagg     120
cctggacagg gtctggaatg gattggcgct gtttctcctg gaaatagtga ctactagctac    180 aaccagaagt tcaagggcaa ggccacactg actgcagtca catccaccag cactgcctac     240

```
atggagttca gcagcctgac aaatgaggac tctgcggtct attactgtac aagaagtcga    300
tatggtaaca atgctttgga ctactggggc caagggacca cggtcaccgt ctcctca       357
```

<210> SEQ ID NO 14
<211> LENGTH: 119
<212> TYPE: PRT
<213> ORGANISM: Mus musculus

<400> SEQUENCE: 14

```
Gln Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Val Ser Pro Gly Asn Ser Asp Thr Ser Tyr Asn Gln Lys Phe
    50                  55                  60

Lys Gly Lys Ala Thr Leu Thr Ala Val Thr Ser Thr Ser Thr Ala Tyr
65                  70                  75                  80

Met Glu Phe Ser Ser Leu Thr Asn Glu Asp Ser Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Thr Val Thr Val Ser Ser
        115
```

<210> SEQ ID NO 15
<211> LENGTH: 330
<212> TYPE: DNA
<213> ORGANISM: Mus musculus

<400> SEQUENCE: 15

```
gacatcgagc tcacccagtc tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240 cctgtgga gg aggaggatgc tgcaacctat tactgtcagc acattaaggg agcttacacg   300
ttcggagggg ggaccaagct ggaaataaaa                                    330
```

<210> SEQ ID NO 16
<211> LENGTH: 330
<212> TYPE: DNA
<213> ORGANISM: Mus musculus

<400> SEQUENCE: 16

```
gacatcgagc tcactcagtc tccagcttct ttggctgtgt ctctagggca gagggccacc    60
atctcctgca gagccagcgc aagtgttgat aattatggca ttagttttat gaactggttc   120
caacagaaac caggacagcc acccaaactc ctcatctatg ctgcatccaa ccaaggatcc   180
ggggtccctg ccaggtttag tggcagtggg tctgggacag acttcagcct caacatccat   240
cctatggagg aggatgatac tgcaacctat tactgtcagc acattaaggg agcttacacg   300
ttcggagggg ggaccaagct ggagctgaaa                                    330
```

<210> SEQ ID NO 17
<211> LENGTH: 321

<212> TYPE: DNA
<213> ORGANISM: Mus musculus

<400> SEQUENCE: 17

```
gacatcgagc tcactcagtc tccatcctcc atgtctgtat ctctgggaga cacagtcaac    60
atcacttgcc gtgcaagtca gggcattagc agtaatatag tgtggttgca gcagaaacca   120
gggaagtcat ttaagggcct gatctatcat gggaccaatt tggaagatgg agttccatca   180
aggttcagtg gcagtggatc tggagccgat tattctctca ccatcagcag cctggaatct   240
gaggattttg cagactatta ctgtgtacag tattctcagt ttcctcccac gttcggctcg   300
gggaccaagc tggagctgaa a                                              321
```

<210> SEQ ID NO 18
<211> LENGTH: 107
<212> TYPE: PRT
<213> ORGANISM: Mus musculus

<400> SEQUENCE: 18

```
Asp Ile Glu Leu Thr Gln Ser Pro Ser Ser Met Ser Val Ser Leu Gly
 1               5                  10                  15

Asp Thr Val Asn Ile Thr Cys Arg Ala Ser Gln Gly Ile Ser Ser Asn
            20                  25                  30

Ile Val Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ser Gln Phe Pro Pro
                85                  90                  95

Thr Phe Gly Ser Gly Thr Lys Leu Glu Leu Lys
            100                 105
```

<210> SEQ ID NO 19
<211> LENGTH: 118
<212> TYPE: PRT
<213> ORGANISM: Homo sapiens

<400> SEQUENCE: 19

```
Gln Val Gln Leu Val Gln Ser Gly Ala Glu Val Val Lys Pro Gly Ala
 1               5                  10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Ala Val Ser Pro Gly Asn Ser Asp Thr Tyr Asn Glu Lys Phe
    50                  55                  60

Lys Gly Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Leu Val Thr Val Ser
        115
```

```
<210> SEQ ID NO 20
<211> LENGTH: 118
<212> TYPE: PRT
<213> ORGANISM: Mus musculus

<400> SEQUENCE: 20

Gln Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Val Ser Pro Gly Asn Ser Asp Thr Ser Tyr Asn Gln Lys Phe
    50                  55                  60

Lys Gly Lys Ala Thr Leu Thr Ala Val Thr Ser Thr Ser Thr Ala Tyr
65                  70                  75                  80

Met Glu Phe Ser Ser Leu Thr Asn Glu Asp Ser Ala Val Tyr Tyr Cys
                85                  90                  95

Thr Arg Ser Arg Tyr Gly Asn Asn Ala Leu Asp Tyr Trp Gly Gln Gly
            100                 105                 110

Thr Thr Val Thr Val Ser
        115

<210> SEQ ID NO 21
<211> LENGTH: 107
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asn
            20                  25                  30

Ile Val Trp Tyr Gln Gln Lys Pro Gly Lys Ala Pro Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ser Gln Phe Pro Pro
                85                  90                  95

Thr Phe Gly Gln Gly Thr Lys Leu Glu Ile Lys
            100                 105

<210> SEQ ID NO 22
<211> LENGTH: 98
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 23
<211> LENGTH: 294
<212> TYPE: DNA
<213> ORGANISM: Homo sapiens

<400> SEQUENCE: 23
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gaga           294

<210> SEQ ID NO 24
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 24

Ile Ser Pro Met Phe Gly Thr Pro
1               5

<210> SEQ ID NO 25
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 25

Ile Ile Pro Ile Phe Gly Thr Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Chemically synthesized peptide

<400> SEQUENCE: 26

Ile Ser Pro Ile Phe Gly Thr Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: wherein said Xaa is an Isoleucine or a Serine
<220> FEATURE:
<221> NAME/KEY: MISC_FEATURE

```
<222> LOCATION: (4)..(4)
<223> OTHER INFORMATION: wherein said Xaa is an Isoleucine or a
      Methionine

<400> SEQUENCE: 27

Ile Xaa Pro Xaa Phe Gly Thr Ala
1               5

<210> SEQ ID NO 28
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: wherein said Xaa is a Glycine or a Glutamic
      acid
<220> FEATURE:
<221> NAME/KEY: MISC_FEATURE
<222> LOCATION: (2)..(2)
<223> OTHER INFORMATION: wherein said Xaa is a Glycine or a Valine

<400> SEQUENCE: 28

Xaa Xaa Thr Phe Ser Ser Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: wherein said Xaa is an Isoleucine or a Serine
<220> FEATURE:
<221> NAME/KEY: MISC_FEATURE
<222> LOCATION: (4)..(4)
<223> OTHER INFORMATION: wherein said Xaa is an Isoleucine or a
      Methionine

<400> SEQUENCE: 29

Ile Xaa Pro Xaa Phe Gly Thr Ala
1               5
```

HUMANIZED MONOCLONAL ANTIBODIES AND METHODS OF USE

RELATED APPLICATIONS

This application is a national stage application, filed under 35 U.S.C. §371, of PCT Application No. PCT/US2011/038970, filed on Jun. 2, 2011, which claims the benefit of U.S. Ser. No. 61/350,790, filed on Jun. 2, 2010, the contents of each of which are incorporated herein by reference in their entireties.

INCORPORATION-BY-REFERENCE OF SEQUENCE LISTING

The contents of the text file named "20363-057N01US_ST25.txt", which was created on Nov. 29, 2012 and is 16 KB in size, are hereby incorporated by reference in their entirety.

GOVERNMENT SUPPORT CLAUSE

This invention was made with government support under grant number U01 AI074518 awarded by The National Institutes of Health. The government has certain rights in the invention.

FIELD OF THE INVENTION

This invention relates generally to humanized anti-humanVH1-69 antibodies as well as to methods of using same to augment the immune response to microbial infection.

BACKGROUND OF THE INVENTION

An influenza pandemic represents one of the greatest acute infectious threats to human health. The 1918-1919 influenza pandemic caused an estimated 500,000 deaths in the United States, making it the most fatal event in all of US history. The spread of highly pathogenic avian influenza (HPAI) H5N1 influenza across Asia and now to the Middle East and northern Africa creates a substantial risk for a new pandemic to arise.

Natural variation as well as escape mutants suggests that continued evolution of the virus should impact the decision on which strain(s) should be used for passive and active immunization. Although a number of important epitope mapping and neutralization escape studies have been reported new neutralizing antibodies and related structural studies are needed to develop immunization strategies to develop a "universal vaccine" against a broad range of Group 1 influenza viruses. The challenges to developing a protective vaccine against Group 1 influenza are formidable and new approaches are needed to prevent and treat human infection by an ever changing enemy. There is a need to rapidly develop therapeutic strategies to elicit protective host's immunity, both passively and actively.

SUMMARY OF THE INVENTION

The invention is based upon the discovery of monoclonal antibodies which bind the human immunoglobulin heavy chain variable region germline gene VH1-69. The monoclonal antibody is fully human. In various aspects, the monoclonal antibody is a bivalent antibody, a monovalent antibody, a single chain antibody or fragment thereof. Exemplary monoclonal antibodies include a monoclonal antibody that binds to the same epitope as murine monoclonal antibody G6.

The monoclonal antibodies of the invention can have a binding affinity that is 1 nM or less.

The monoclonal antibody has a heavy chain variable amino acid sequence containing SEQ ID NOS: 2 or 12, and/or a light chain variable amino acid sequence containing SEQ ID NO: 4. The monoclonal antibody has a heavy chain variable nucleic acid sequence containing SEQ ID NOS: 1 or 11, and/or a light chain variable nucleic acid sequence containing SEQ ID NO: 3.

Also provided by the invention is a monoclonal human immunoglobulin heavy chain variable region germline gene VH1-69 antibody or fragment thereof, where the antibody has a CDRH1: GYTFTSYW (SEQ ID NO: 5); CDRH2: VSPGNSDT (SEQ ID NO: 6); and CDRH3: TRSRYGN-NALDY (SEQ ID NO: 7) and a CDRL1: QGISSNIVW (SEQ ID NO: 8); CDRL2: HGT (SEQ ID NO: 9); and CDRL3: VQYSQFPPT (SEQ ID NO: 10).

In some aspects the antibody according to the invention is covalently linked to an antigen. The antibody is preferably a single chain antibody and the antigen is the stem region of the hemagglutinin (HA) protein of an influenza virus.

Also included in the invention are methods of augmenting the immune response of a subject to an antigen by administering to the subject an anti-immunoglobulin variable region germline gene idiotype antibody and an immunogen capable of inducing an immune reaction to the antigen. In some aspects the antibody is covalently linked to the antigen. The germline gene encodes for a light chain polypeptide or a heavy chain polypeptide. Preferably, the variable region germline gene is VH1-69. The antigen is a virus, a bacterium, or a fungus. For example the virus is an influenza virus. Preferably, the immunogen is the hemagglutinin (HA) protein of an influenza virus or fragment thereof. Most preferably, the immungen contains the stem region of the hemagglutinin (HA) protein of an influenza virus. The antibody can be administered prior to, concurrently with, or subsequent to the administration of the immunogen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 3 shows the homology model of Human G6.1 antibody VH and VL. a), Human G6.1 antibody model, VH in blue and VL in green with CDRs in red. b), Human G6.1 homology model after GROMOS force field energy minimization, visualized in DeepView program, highlighted in different colors are residues exhibiting either distorted geometry or steric clashes.

FIG. 13 shows main germline nucleotide codons that distinguish the different variants of the VH1-69 gene. Among 13 alleles, alleles *01, *03, *05, *06, *12, and *13 are 51p1 related.

DETAILED DESCRIPTION

Figure 1:
FIG. 1 shows homology model of mouse G6 antibody heavy chain (VH) and light chain (VL) generated using Web antibody modeling (WAM). VH colored in blue and VL colored in green with CDRs highlighted in red.

The present invention provides humanized monoclonal antibodies specific against human immunoglobulin heavy chain variable region germline gene VH1-69. In particular, the invention provides a humanized anti-human VH1-69 idiotype antibody G6 (referred to herein as huG6). More specifically, the invention provides a method of augmenting an immune response to an antigen by focusing an immune response to a human variable region germline gene in combination with antigenic stimulation.

Specifically, this invention is based upon a previous work in which high affinity, cross-subtype, broadly-neutralizing human anti-hemagglutinin mAbs were identified. (See, WO 2009/086514 and WO 2011/027818, the contents of which are hereby incorporated by reference in their entireties.) A human antibody phage display library and H5 hemagglutinin (HA) ectodomain was used to select ten neutralizing mAbs (nAbs) with a remarkably broad range among Group 1 influenza viruses, including the H5N1 "bird flu" and the H1N1 "Spanish flu" and "Swine flu" strains. These nAbs inhibit the post-attachment fusion process by recognizing a novel and highly conserved neutralizing epitope (referred to herein as the F10 epitope) within the stem region at a point where key elements of the conformational change—the fusion peptide and the exposed surface of helix αA—are brought into close apposition.

Remarkably, these isolated nAbs utilizes the same VH germline gene, IGHV1-69*01, and encodes a CDR3 loop containing a tyrosine at an equivalent position to Y102, from a non-immune library. This indicated that broad anti-HA cross-immunity pre-exists in the H5-naive population. The recurrent use of this germline VH segment, the commonality of the CDR3 tyrosine introduced through N insertion and/or germline D gene assembly, and the promiscuous use of VL genes by the discovered nAbs discovered indicate that the precursor frequency of rearranged VH segments that could recognize this epitope is significant. This indicates that with suitable exposure to the F10 epitope, these broad-spectrum nAbs can be readily induced in vivo.

The hemagglutinin of the influenza virus has to functions that are essential for the initiation of the influenza virus infection and involve two structurally distinct regions, the globular head and the stem region. The globular head region contains the main antigenic determinants in which the antigenic mutations arise. The stem region however is conserved. Thus, finding of these broadly-neutralizing human anti-hemagglutinin mAbs suggest that with proper antigenic stimulation, humans are capable of eliciting broad neutralizing anti-influenza response.

Anti-idiotype antibodies (termed Ab2) are antibodies directed against the variable region (antigen-binding site) of another antibody (Ab1), the idiotype. In turn, immunization with Ab2 antibodies can induce antibodies with specificities similar to the original antibodies. In the present invention it is proposed to immunize with an anti-idiotypic antibody that is specific for immunoglobulin variable region germline gene to clonotypically stimulate a germline gene immune response. This will in effect prime the immune system by activating germline gene specific B-cells.

Accordingly, in one aspect the invention provides a method or augmenting an immune response in a subject to an antigen by administering to the subject an anti-immunoglobulin variable region germline gene idiotype antibody and an immunogen capable of inducing an immune reaction to the antigen. For example, the variable region germline gene is VH1-69.

In another aspect the present invention provides a humanized monoclonal antibody that specifically binds human immunoglobulin heavy chain variable region protein encode by germline gene VH1-69. The huG6 antibody is monovalent or bivalent and comprises a single or double chain. Functionally, the binding affinity of the huG6 antibody is less than 250 nM, less than 100 nM, less than 10 nM, less than 1 nM, or less than 100 pM. Preferably, the binding affinity is within a range of 100 pM-1 nM. The sequence of the antibody is engineered from and thus, may comprises one or more antigen-binding regions of murine antibody G6. The huG6 antibody binds the same epitope as murine Mab G6. Furthermore, the antibody comprises an immungen (i.e., antigen) including, but not limited to, the hemagglutinin (HA) protein of an influenza virus or fragment thereof. For example, the immunogen comprises the stem region of the hemagglutinin (HA) protein of an influenza virus.

The murine G6 (muG6) single-chain antibody (1567) was constructed from the hybridoma cell clone G6. Upon cloning, it was discovered that the G6 hybridoma encoded three different variable light chain genes. All the light chains were Vk. The murine G6 VH and VL nucleic acid and amino acid sequences are as follows:

```
muG6 VH nucleotide sequence:
                                                              (SEQ ID NO: 13)
CAGGTCCAGCTGCAGCAGTCTGGGACTGTGCTCGCAAGGCCTGGGGCTTCAGTGAAGATGTCCTGCAAGGCTTCT

GGCTACACCTTTACCAGTTACTGGATGCACTGGGTAAAACAGAGGCCTGGACAGGGTCTGGAATGGATTGGCGCT

GTTTCTCCTGGAAATAGTGATACTAGCTACAACCAGAAGTTCAAGGGCAAGGCCACACTGACTGCAGTCACATCC

ACCAGCACTGCCTACATGGAGTTCAGCAGCCTGACAAATGAGGACTCTGCGGTCTATTACTGTACAAGAAGTCGA

TATGGTAACAATGCTTTGGACTACTGGGGCCAAGGGACCACGGTCACCGTCTCCTCA muG6 VH amino acid sequence:
                                                              (SEQ ID NO: 14)
QVQLQQSGTVLARPGASVKMSCKASGYTFTSYWMHWVKQRPGQGLEWIGAVSPGNSDTSYNQKFKGKATLTAVTS

TSTAYMEFSSLTNEDSAVYYCTRSRYGNNALDYWGQGTTVTSS muG6-19 V_L nucleotide sequence:
                                                              (SEQ ID NO: 15)
GACATCGAGCTCACCCAGTCTCCTGCTTCCTTAGCTGTATCTCTGGGGCAGAGGGCCACCATCTCATACAGGGCC

AGCAAAAGTGTCAGTACATCTGGCTATAGTTATATGCACTGGAACCAACAGAAACCAGGACAGCCACCCAGACTC

CTCATCTATCTTGTATCCAACCTAGAATCTGGGGTCCCTGCCAGGTTCAGTGGCAGTGGGTCTGGGACAGACTTC

ACCCTCAACATCCATCCTGTGGAGGAGGAGGATGCTGCAACCTATTACTGTCAGCACATTAagGGAGCTTACACG
```

TTCGGAGGGGGGACCAAGCTGGAAATAAAA muG6-30 V$_L$ nucleotide sequence:
(SEQ ID NO: 16)
GACATCGAGCTCACTCAGTCTCCAGCTTCTTTGGCTGTGTCTCTAGGGCAGAGGGCCACCATCTCCTGCAGAGCC

AGCGCAAGTGTTGATAATTATGGCATTAGTTTTATGAACTGGTTCCAACAGAAACCAGGACAGCCACCCAAACTC

CTCATCTATGCTGCATCCAACCAAGGATCCGGGGTCCCTGCCAGGTTTAGTGGCAGTGGGTCTGGGACAGACTTC

AGCCTCAACATCCATCCTATGGAGGAGGATGATACTGCAACCTATTACTGTCAGCACATTAaGGGAGCTTACACG

TTCGGAGGGGGGACCAAGCTGGAGCTGAAA muG6-39 V$_L$ nucleotide sequence:
(SEQ ID NO: 17)
GACATCGAGCTCACTCAGTCTCCATCCTCCATGTCTGTATCTCTGGGAGACACAGTCAACATCACTTGCCGTGCA

AGTCAGGGCATTAGCAGTAATATAGTGTGGTTGCAGCAGAAACCAGGGAAGTCATTTAAGGGCCTGATCTATCAT

GGGACCAATTTGGAAGATGGAGTTCCATCAAGGTTCAGTGGCAGTGGATCTGGAGCCGATTATTCTCTCACCATC

AGCAGCCTGGAATCTGAGGATTTTGCAGACTATTACTGTGTACAGTATTCTCAGTTTCCTCCCACGTTCGGCTCG

GGGACCAAGCTGGAGCTGAAA muG6 V$_L$ amino acid sequence:
(SEQ ID NO: 18)
DIELTQSPSSMSVSLGDTVNITCRASQGISSNIVWLQQKPGKSFKGLIYHGTNLEDGVPSRFSGSGSGADYSLTI

SSLESEDFADYYCVQYSQFPPTFGSGTKLELK

The heavy chain CDRs of the huG6 antibody have the following sequences: CDRH1: GYTFTSYW (SEQ ID NO: 5); CDRH2: VSPGNSDT (SEQ ID NO: 6); and CDRH3: TRSRYGNNALDY (SEQ ID NO: 7). The light chain CDRs of the huG6 antibody have the following sequences: CDRL1: QGISSNIVW (SEQ ID NO: 8); CDRL2: HGT (SEQ ID NO: 9); and CDRL3: VQYSQFPPT (SEQ ID NO: 10). The nucleotide VH and VL sequences were optimized for mammalian codon usage.

huG6.2 V$_H$ nucleotide sequence:
(SEQ ID NO: 1)
CAGGTCCAGCTCGTCCAGTCCGGCGCTGAAGTGGTGAAACCCGGGGCATCCGTCAAAGTCTCTTGTAAGGCTAGT

GGCTACACCTTCACATCCTACTGGATGCATTGGGTGAAACAGGCACCTGGCCAGGGACTCGAATGGATCGGAGCC

GTGTCTCCTGGAAATTCCGACACCTCCTACAACGAAAAATTCAAGGGCAAGGCAACCCTCACTGTGGATACTAGT

GCTTCTACCGCCTACATGGAACTCTCATCTCTCCGCTCTGAGGACACTGCCGTCTACTACTGTACTCGGTCACGA

TACGGGAACAACGCTCTCGATTACTGGGGACAGGGCACACTGGTCACTGTCTCT huG6.2 V$_H$ amino acid sequence:
(SEQ ID NO: 2)
QVQLVQSGAEVVKPGASVKVSCKASGYTFTSYWMHWVKQAPGQGLEWIGAVSPGNSDTSYNEKFKGKATLTVDTS

ASTAYMELSSLRSEDTAVYYCTRSRYGNNALDYWGQGTLVTVS huG6.2 V$_L$ and huG6.3 V$_L$ nucleotide sequence:
(SEQ ID NO: 3)
GATATTCAGCTCACACAGAGCCCATCTTCTCTGTCTGCTTCTGTGGGCGATCGAGTGACAATCACTTGTCGGGCT

AGTCAGGGCATTTCTAGCAACATTGTGTGGCTCCAGCAGAAACCTGGCAAAGCCCCAAAAGGCCTCATCTACCAC

GGAACCAACCTGGAATCTGGCGTGCCATCTCGGTTTAGTGGATCTGGATCCGGGACCGATTACACACTCACCATC

TCTTCACTGGAACCTGAGGATTTCGCCACCTACTACTGTGTCCAGTACTCCCAGTTTCCACCCACTTTTGGACAG

GGAACCAAACTCGAGATCAAA huG6.2 V$_L$ and huG6.3 V$_L$ amino acid sequence:
(SEQ ID NO: 4)
DIQLTQSPSSLSASVGDRVTITCRASQGISSNIVWLQQKPGKAPKGLIYHGTNLESGVPSRFSGSGSGTDYTLTI

SSLEPEDFATYYCVQYSQFPPTFGQGTKLEIK huG6.3 V$_H$ nucleotide sequence:

-continued

```
                                                              (SEQ ID NO: 11)
CAGGTCCAGCTCGTCCAGTCCGGCGCTGAAGTGGTGAAACCCGGGGCATCCGTCAAAGTCTCTTGTAAGGCTAGT

GGCTACACCTTCACATCCTACTGGATGCATTGGGTGAAACAGGCACCTGGCCAGGGACTCGAATGGATCGGAGCC

GTGTCTCCTGGAAATTCCGACACCTCCTACAACGAAAAATTCAAGGGCAAGGCAACCCTCACTGTGGACAAATCT

GCCTCTACCGCCTACATGGAACTCTCATCTCTCCGCTCTGAGGATACTGCTGTGTACTACTGTACCCGGTCACGA

TACGGCAATAACGCCCTCGATTACTGGGGGCAGGGAACTCTGGTCACTGTGTCT huG6.3 V_H amino acid sequence:
                                                              (SEQ ID NO: 12)
QVQLVQSGAEVVKPGASVKVSCKASGYTFTSYWMHWVKQAPGQGLEWIGAVSPGNSDTSYNEKFKGKATLTVDKS

ASTAYMELSSLRSEDTAVYYCTRSRYGNNALDYWGQGTLVTVS
```

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$::$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." Specifically, the CDRs of the antibody heavy chains are referred to as CDRH1, CDRH2 and CDRH3, respectively. Similarly, the CDRs of the antibody light chains are referred to as CDRL1, CDRL2 and CDRL3, respectively.

An idiotype is the genetically determined variation of intramolecular structures in the variable regions of immunoglobulins. T. However, idiotype variation involves the amino acid sequence and protein structure (so-called determinants) especially in the area of the antigen-binding site, also referred to as the "idiotope". The term "idiotype" designates the complete set of determinants of a variable region of an antibody molecule.

An anti-idiotype antibody may be generated with a process that uses a purified human monoclonal antibody or a human hybridoma cell line that expresses a human monoclonal antibody. For example a process for generation of an anti-idiotype antibody may involve culturing a human hybridoma cell line that secretes a human monoclonal antibody into its supernatant and purifying this antibody, for example, using affinity chromatography, ion exchange chromatography, gel filtration, or a combination thereof. This purified human monoclonal antibody may then be used to immunize a non-human mammal, such as a mouse or a rat, by means of, for instance, an intraperitoneal injection or in vitro directly on isolated B lymphocytes. B lymphocytes may then be isolated from the non-human mammal sacrificed up to four days after the last immunization, and the isolated B lymphocytes may be brought into contact with myeloma cells of same species (e.g., mouse or rat) under conditions that lead to fusion of the myeloma cells with the B lymphocytes to generate a non-human hybridoma cell. These non-human hybridoma cells can then be cultured and tested (e.g., using ELISA) for expression of idiotype Ig antibodies, e.g., IgM, IgA, or IgG antibodies, after, for example, three weeks of culturing. These Ig antibodies can be tested for specific binding to the human hybridoma cells and to various antibodies, including the human monoclonal antibody used to immunize the non-human mammal.

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an epitope when the equilibrium binding constant ($K_d$) is ≤1 μM, preferably ≤100 nM, more preferably ≤10 nM, and most preferably ≤100 pM to about 1 pM, as measured by assays such as radioligand binding assays or similar assays known to those skilled in the art.

Those skilled in the art will recognize that it is possible to determine, without undue experimentation, if a human monoclonal antibody has the same specificity as a human monoclonal antibody of the invention by ascertaining whether the former prevents the latter from binding to a human immunoglobulin variable region polypeptide. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal*

*Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adenoassociated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

Techniques can be adapted for the production of singlechain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl)carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxy-sulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Methods of Treatment

The antibodies can be used to prevent, diagnose, or treat medical disorders in a subject, especially in humans. The invention provides for both prophylactic and therapeutic methods of treating a subject at risk of (or susceptible to) or having an infection. The infection is viral, bacterial, fungal, or parasitic.

The present invention provides methods of augmenting the immune response of a subject to an antigen comprising administering to said subject an antibody or fragment thereof that recognizes a human heavy chain variable region germline geneVH1-69 and an immunogen capable of inducing an immune reaction to said antigen. In some aspects the antibody is huG6.2. In another aspect, the antibody is huG6.3. In some aspect the antibody includes a heavy chain variable region (SEQ ID NOS: 2 or 12), encoded by the nucleic acid sequence SEQ ID NOS: 1 or 11, and a light chain variable region (SEQ ID NO: 4) encoded by the nucleic acid sequence SEQ ID NO: 3. The heavy chain CDRs of the antibody have the following sequences: SEQ ID NOS: 5, 6 and 7. The light chain CDRs of the antibody have the following sequences: SEQ ID NOS: 8, 9 and 10. Preferably the three heavy chain CDRs include an amino acid sequence of at least 90%, 92%, 95%, 97%, 98%, 99%, or more identical to the amino acid sequence of SEQ ID NOS: 5, 6 and 7 and a light chain with three CDRs that include an amino acid sequence of at least 90%, 92%, 95%, 97%, 98%, 99%, or more identical to the amino acid sequence of SEQ ID NOS: 8, 9 and 10.

In some aspects, the immunogen is covalently linked to the antibody. The antigen could be a virus, a bacterium, a fungus, or a parasite. The immunogen is of viral (e.g. influenza, HIV), bacterial, fungal origin. For example, the immunogen is the hemagglutinin (HA) protein of an influenza virus or fragment thereof. Preferably, the immunogen comprises the stem region of the hemagglutinin (HA) protein of an influenza virus. The antibody of this invention can be administered prior to, concurrently with, or subsequent to the administration of the immunogen.

Included in the invention are methods of increasing or enhancing an immune response to an antigen. An immune response is increased or enhanced by administering to the subject an anti-immunoglobulin variable region germline gene idiotype antibody and an immunogen. In a preferred embodiment, the antibody includes a heavy chain variable region (SEQ ID NOS: 2 or 12), encoded by the nucleic acid sequence SEQ ID NOS: 1 or 11, and a light chain variable region (SEQ ID NO: 4) encoded by the nucleic acid sequence SEQ ID NO: 3. The heavy chain CDRs of the antibody have the following sequences: SEQ ID NOS: 5, 6 and 7. The light chain CDRs of the antibody have the following sequences: SEQ ID NOS: 8, 9 and 10. Preferably the three heavy chain CDRs include an amino acid sequence of at least 90%, 92%, 95%, 97%, 98%, 99%, or more identical to the amino acid sequence of SEQ ID NOS: 5, 6 and 7 and a light chain with three CDRs that include an amino acid sequence of at least 90%, 92%, 95%, 97%, 98%, 99%, or more identical to the amino acid sequence of SEQ ID NOS: 8, 9 and 10.

In some embodiments the germline gene is VH1-69. In some aspects the antibody is huG6.2. In another aspect, the antibody is huG6.3. The antigen could be a virus, a bacterium, a fungus, or a parasite. The immunogen is of viral (e.g. influenza, HIV), bacterial, fungal origin. For example, the immunogen is the hemagglutinin (HA) protein of an influenza virus or fragment thereof. Preferably, the immunogen comprises the stem region of the hemagglutinin (HA) protein of an influenza virus. The antibody of this invention can be administered prior to, concurrently with, or subsequent to the administration of the immunogen.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention further pertains to novel agents identified by any of the aforementioned screening assays and uses thereof for treatments as described herein.

All of the above U.S. patents, U.S. patent application publications, U.S. patent applications, and foreign patents, foreign patent applications referred to in this specification, are incorporated herein by reference in their entirety.

All publications cited in the specification are indicative of the level of skill of those skilled in the art to which this invention pertains. All these publications are herein incorporated by reference in their entirety to the same extent as if each individual publication were specifically and individually indicated to be incorporated by reference.

EXAMPLES

Example 1

Humanization of Mouse G6 Antibody

1. Homology Model of Mouse G6 Antibody Using Web Antibody Modeling (WAM).

Mouse G6 variable heavy (VH) and variable light (VL) chain amino acid sequence were submitted to Web based Antibody Modeling program (WAM)[1] for generating the homology model of mouse G6 antibody. The WAM program takes into account various parameters which govern different conformations of the antibodies. In antibodies, usually the residues in the framework region are found to be mostly conserved whereas the residues which form the complementary determining regions (CDRs) are the most variable. As such homology based approach is used, five of the six CDRs (except Heavy chain CDR3) can be categorized into classical canonical structure classes. In addition, members of the same canonical classes have very similar loop conformation. This is determined by the length of the loop, presence of certain conserved key residues not only in framework regions but also in the CDRs.

Briefly WAM carried out different computational parameters in its algorithm to create a homology model of mouse G6 antibody format from its amino acid sequence using the following criteria:

a) The framework residues of a mouse G6 antibody which not only includes backbone residues but also side chain residues together with canonical loop backbone residues were built using the most known (X-ray and NMR) homology structures.

b) Using uniform conformational sampling with iterative algorithm CONGEN, predicted the conformation of side chains in the loops as to obtain the most energetically minimized conformation[2].

c) The non-canonical loop regions were modeled through a series of conformations obtained from protein data bank database search (PDB) or using different conformational/structure based database search for a loop conformation.

d) The different conformations generated using the previous step was further energy minimized using Eureka, which is a solvent-modified version of Valence Force field (VFF)[3]). In addition, root mean square deviation (R.M.S.D) screen which compares similarity in the r.m.s.d to the known heavy chain CDR3 (H3) structures containing same length as the modeling candidate was also used.

The final model of mouse G6 antibody was selected from the first five lowest energy conformations. The algorithm compared the torsion angles between the model candidate and the original set of loops from a known structure in protein data bank. The final model with conformation closest to the set of torsion angles was selected and displayed in FIG. 1.

2. Humanization of Mouse G6 and Generation of the 1$^{st}$ Version of Humanized G6 (huG6.1) on the Basis of G6's Closest Human Germline Sequence and Surface Accessibility of Residues in Frameworks of Mouse G6 Homology Model The mouse G6 homology model generated from WAM was used as a template to identify residues which are surface accessible (solvent exposed) as visualized through Deep-View program, using a 30% threshold limit[4-5]. Subsequently mouse G6 variable heavy chain (VH) and light chain (VL) residues were searched using IGBLAST (www.ncbi.nlm.nih.gov/igblast/) against the human IgG germline database. To humanize mouse G6, we exchanged the surface accessible residues in frameworks of both VH and VL manually to those found in the selected human germline sequence, thus generating humanized G6 version 1 (hG6.1). Sequence alignment is shown below (Total 14 amino acids changes in VH, and 15 in VL).

```
VH
(SEQ ID NO: 19)  Human-G6.1-VH  QVQLVQSGAEVVKPGASVKVSCKASGYTFTSYWMHWVKQAPGQGLEWIGAVSPGNSDTSY
(SEQ ID NO: 20)  Mouse-G6-VH    QVQLQQSGTVLARPGASVKMSCKASGYTFTSYWMHWVKQRPGQGLEWIGAVSPGNSDTSY
                                **** ***  : .:****** :********************* *******************

(SEQ ID NO: 19)  Human-G6.1-VH  NEKFKGKATLTVDKSASTAYMELSSLRSEDTAVYYCTRSRYGNNALDYWGQGTLVTVS
(SEQ ID NO: 20)  Mouse-G6-VH    NQKFKGKATLTAVTSTSTAYMEFSSLTNEDSAVYYCTRSRYGNNALDYWGQGTTVTVS
                                *.********* .*:******:***  **.************************ ****

VL
(SEQ ID NO: 21)  Human-G6.1-VL  DIQMTQSPSSLSASVGDRVTITCRASQGISSNIVWYQQKPGKAPKGLIYHGTNLESGVPSRF
(SEQ ID NO: 18)  Mouse-G6-VL    DIELTQSPSSMSVSLGDIVNITCRASQGISSNIVWLQQKPGKSPKGLIYHGTNLEDGVPSRF
                                **:*******:*.*:** *.********************: ***********.******

(SEQ ID NO: 21)  Human-G6.1-VL  SGSGSGTDYTLTISSLQPEDFATYYCVQYSQFPPTFGQGTKLEIK
(SEQ ID NO: 18)  Mouse-G6-VL    SGSGSGADYSLTISSLESEDFADYYCVQYSQFPPTFGSGTKLELK
                                ******.**.*******.****.************** ***** *
```

Figure 2:
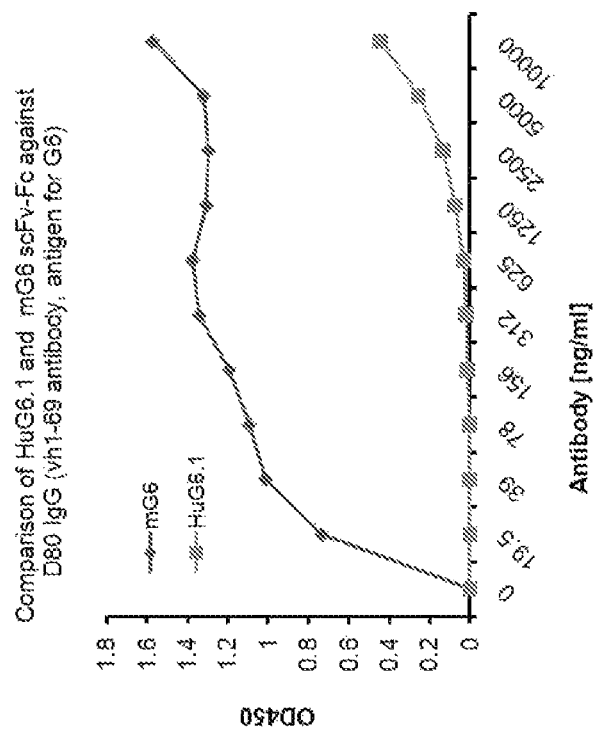
FIG. 2 shows the comparison of antigen binding activity of huG6.1 and mG6 antibodies.

Next, human G6.1 single chain variable region (scFv) was de novo synthesized by Genewiz and the gene was codon-optimized for mammalian cell expression. The scFv-Fc fragment of huG6.1 was constructed by subcloning the synthesized scFv into a Fc expression vector pcDNA3.1-Hinge which contains the hinge, CH2 and CH3 domains of human IgG1 but lacks CH1 domain. Human G6.1 scFv-Fc was expressed in 293T cells (ATCC) by transient transfection (Lipofectamine, Invitrogen) and purified by protein A sepharose affinity chromatography. To test the antigen (herein is D80-IgG1 that uses the 51p1 form of VH1-69) binding activity of huG6.1 scFv-Fc and compare it with mouse G6, we biotinylated huG6.1 and mouse G6 with a commercial biotinylation kit (Pierce) and did ELISA analysis. Briefly, D80-IgG was coated on to a 96 well Maxisorp plate at 2 μg/ml, overnight at 4° C. Unbound protein was washed away with PBS and the plate was blocked with 2% milk/PBS for 1 hour at 25° C. Diluted biotinylated HuG6.1 scFv-Fc and Mouse G6 scFv-Fc was added to the wells and incubated at 25° C. for 1 hour. Plates were washed with PBST (0.05% Tween/PBS). Streptavidin-HRP was added, incubated at 25° C. for 30 minutes. Plates were washed again and developed with TMB solution and 5 minutes later reaction was stopped with addition of stop reagent. Plate was read at OD450. As shown in FIG. 2, huG6.1 lost antigen binding activity significantly as compared to mouse G6 (FIG. 2)

3. Energy Minimization of huG6.1 to Improve the Humanization.

Next, we applied GROMOS force field energy minimization parameter to homology model huG6.1 using DeepView program[6]. The final model was visualized with DeepView and PyMOL programs as shown in FIG. 3a. Examination of this energy minimized homology model of Human G6.1 resulted in the identification of certain residues which had distorted geometry or steric clashes between different residues in framework as well as complementary determining region residues (CDRs) as shown in FIG. 3b.

4. Generate huG6.2 and G6.3 Antibody in Order to Ameliorate Distorted Geometry and Steric Clashes Using PyMOL Program.

Figure 4:
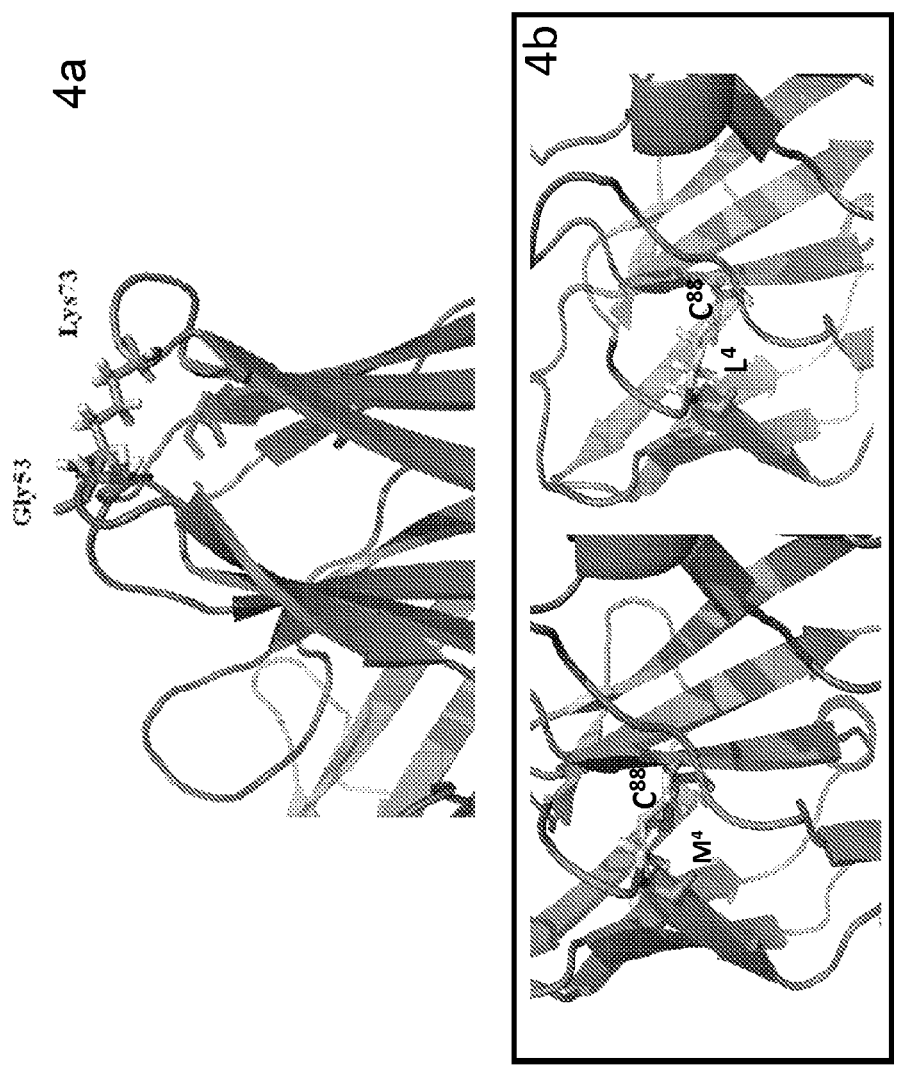
FIG. 4 displays residues with distorted geometry and steric clashes between residues within framework regions as well as between framework and CDR residues using Pymol program.

Closer examination in DeepView program displayed certain residues with high entropy in their side chain rotamers. These anomalies revealed residues with distorted geometry and steric clashes between residues within framework regions as well as between framework and CDR residues. Further inspection in PyMOL led to the following observations:

i) Lysine$^{73}$ (Lys$^{73}$) (kabat numbering being followed throughout) in the VH steric clashed with Glycine$^{53}$ (Gly$^{53}$) in CDR2 of VH (FIG. 4a). Because CDR residues should not be changed, the Lys$^{73}$ (in huG6.3) was changed back to Thr of mouse G6 to solve the steric clash.

ii) Methionine$^{4}$ (Met$^{4}$) had a steric clash with the conserved cysteine$^{88}$ (Cys$^{88}$) residue which is positioned right before CDR3 of the light chain variable region as shown in left panel in FIG. 4b. Sequence alignment revealed that Cys$^{88}$ is highly conserved residue and Met$^{4}$ is not, therefore Met$^{4}$ can be backmutated to Leucine residue as found in mouse G6. This back mutation solved the steric clash between the residues as shown in the right panel in FIG. 4b.

iii) Tyrosine$^{36}$ (Tyr$^{36}$) in the light chain framework 2 also had steric clash with Leucine$^{100B}$ (Leu$^{100B}$) in the CDR3 of heavy chain the left panel FIG. 4c. As such Tyr$^{36}$ can be back mutated to Leu$^{36}$ (mouse residue) which solves the steric clash between the residues as shown in right panel in FIG. 4c.

iv) Glutamine$^{79}$ (Gln$^{79}$) residue in framework 3 (light chain) region had steric clash with Arginine$^{61}$ (Arg$^{61}$) of the same framework left panel in FIG. 4d. Sequence alignment indicated that Arg$^{61}$ is mostly conserved among different homologous sequences whereas Gln$^{79}$ was not conserved. As such Gln$^{79}$ can be back mutated to Glutamate$^{79}$ in the light chain which fixes the steric clash as shown in right panel in FIG. 4d.

In summary, we identified four residues which can be changed back to mouse residues: one residue in VH (Thr73) and three residues in VL (Leu4, Leu36, Glu79). Based on this structural analysis result, we made humanized G6 version 2 (huG6.2) and version 3 (huG6.3). In huG6.2, the four residues were changed back to mouse residues. In huG6.3, only the 3 amino acids in VL were changed back to mouse residues, in another words, there is only one amino acid difference between huG6.2 and huG6.3 which is mouse residue Thr73 in VH of huG6.2, while human Lys73 in VH of huG6.3. The amino acid sequence differences among the huG6.1, huG6.2, huG6.3 and mouse G6 genes are shown below, highlighted in pink are the four residues.

Multiple Sequence Alignment of huG6.1, huG6.2, huG6.3 and Mouse G6.

```
VH
(SEQ ID NO: 19)   Human-G6.1-VH   QVQLVQSGAEVVKPGASVKVSCKASGYTFTSYWMHWVKQAPGQGLEWIGAVSPGNSDTSY
(SEQ ID NO: 2)    Human-G6.2-VH   QVQLVQSGAEVVKPGASVKVSCKASGYTFTSYWMHWVKQAPGQGLEWIGAVSPGNSDTSY
(SEQ ID NO: 12)   Human-G6.3-VH   QVQLVQSGAEVVKPGASVKVSCKASGYTFTSYWMHWVKQAPGQGLEWIGAVSPGNSDTSY
(SEQ ID NO: 20)   Mouse-G6-VH     QVQLQQSGTVLARPGASVKMSCKASGYTFTSYWMHWVKQRPGQGLEWIGAVSPGNSDTSY
                                  ****.***.:..:******.***********************.***************

(SEQ ID NO: 19)   Human-G6.1-VH   NEKFKGKATLTVDKGASTAYMELSSIRSEDTAVYYCTRSRYGNNALDYWGQGTLVTVS
(SEQ ID NO: 2)    Human-G6.2-VH   NEKFKGKATLTVDTSASTAYMELSSLRSEDTAVYYCTRGRYGNNALDYWGQGTVTSVS
(SEQ ID NO: 12)   Human-G6.3-VH   NEKEKGKATLTVDKGASTAYMELSSLRGEDTAVYYCTRSRYGNNALDYWGQGTLVTVS
(SEQ ID NO: 20)   Mouse-G6-VH     NQKEKGKATLTAVTGTSTAYMEFSSLTNELNAVYYCTRSRYGNMALDYWGQGTTVTVS
                                  *:*********.*:*:******:***.**.:*********** ************.****

VL
(SEQ ID NO: 21)   Human-G6.1-VL   DIQMTQSPSSLSASVGDRVTITCRASQGISSNIVWYQQKPGKAPKGLIYHGTNLESGVPSRF
(SEQ ID NO: 4)    Human-G6.2-VL   DIQLTQSPSSLSASVGDRVTITCRASQGISSNIVWLQQKPGKAPKGLIYRGTNLESGVPSRF
(SEQ ID NO: 4)    Human-G6.3-VL   DIQLTQSPSSLSASVGDPVTITCRASQGISSNIVWLQQKPGKAPKGLIYHGTNLESGVPSRF
(SEQ ID NO: 18)   Mouse-G6-VL     DIELTQSPSSNSMSLGDTVNITCRASQGISSNIVWLQQKPGKNFKGLIYWGTNLESGVPSRF
                                  **:*******.*.*:**.*.**********************: ********.*******

(SEQ ID NO: 21)   Human-G6.1-VL   SGSGSGTDYTLTISSLQPEDFATYYCVQYSQFPPTFGQGTKLEIK
(SEQ ID NO: 4)    Human-G6.2-VL   SGSGSGTDYTLTISSLEPEDFATYYCVQYSQFPPTFGQGTKLEIK
(SEQ ID NO: 4)    Human-G6.3-VL   SGSGSGTDYTLTISSLEPEDFATYYCVQYSQFPPTFGQGTKLEIK
(SEQ ID NO: 18)   Mouse-G6-VL     SGSGSGNDYPLTISSLESEDFADYYCVQYSQFPPTFGSGTKLELK
                                  ******:**:******* ****.************* ******:*
```

5. Comparing Antigen Binding Activity of huG6.2 and Mouse G6.

Figure 5:
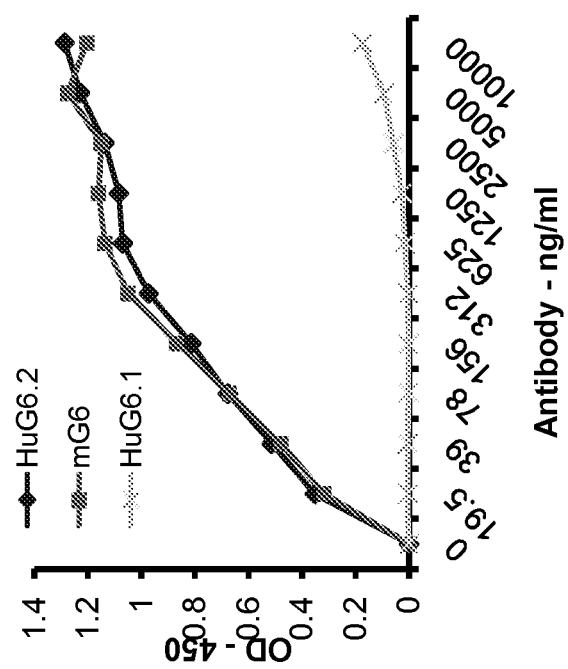
FIG. 5 shows the comparison of antigen binding activity of huG6.2 and mG6 scFv-Fc.

Human G6.2 scFv-Fc was synthesized, expressed, purified and biotinylated using the same method as described above for huG6.1. ELISA was performed to compare huG6.2 and mouse G6. As shown in FIG. 5, huG6.2 has similar binding activity to D80 as the mouse G6. Also it is consistent with the data shown in FIG. 2, huG6.1 only binds very weakly to D80. This demonstrated that the four residue changes from huG6.1 back to mouse residues—huG6.2 indeed play critical important role in restoring the binding activity of humanized G6.

Figure 6:
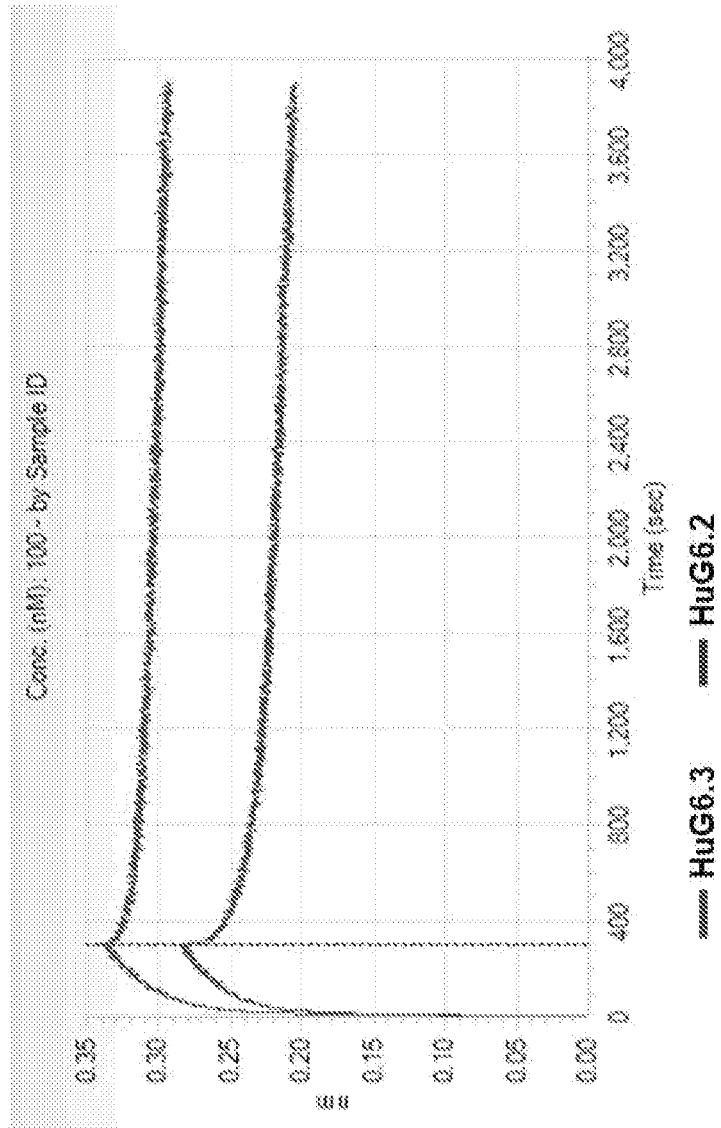
FIG. 6 is a Real time Bio-Layer Interferometry binding analysis of HuG6.2(Red) and Mouse G6(Blue) to the biotinylated D80 scFv-Fc.

We also compared huG6.2 scFv-Fc and mG6 scFv-Fc using Octet Red instrument (ForteBio, Menlo Park, Calif., USA) that utilize Bio-Layer Interferometry (BLI), a label-free technology to measure protein-protein interaction. For this assay, Antigen for G6, D80-scFv-Fc, was biotinylated and coated on streptavidin (SA) biosensor tips (ForteBio, Menlo Park, Calif., USA). The assay was performed at 30° C. in 1× kinetics assay buffer (0.1 mg/ml BSA, 0.002% Tween-20, PBS). Samples were agitated at 1000 rpm. Prior to experimental run, the SA sensors were humidified in PBS for 15 minutes. SA sensor tips were loaded with 20 μg/ml of biotinylated D80 scFv-Fc for 900 secs which typically resulted in capture levels of 3.0-3.5 nM. G6 antibodies were prepared in 100 nM concentration. Association and dissociation rates were monitored for 300 secs. Data was processed and analyzed using the Octet data analysis software (ForteBio). As shown in FIG. 6. HuG6.2 (red) has a slower association and dissociation rates than that of mouse G6 (blue). The affinity for both are within a range of 100 pM-1 nM.

6. Kinetic Analysis of the Binding Activity of HuG6.2 scFv-Fc and HuG6.3 (Thr73Lys mutant) scFv-Fc to Biotinylated D80.

Figure 7:
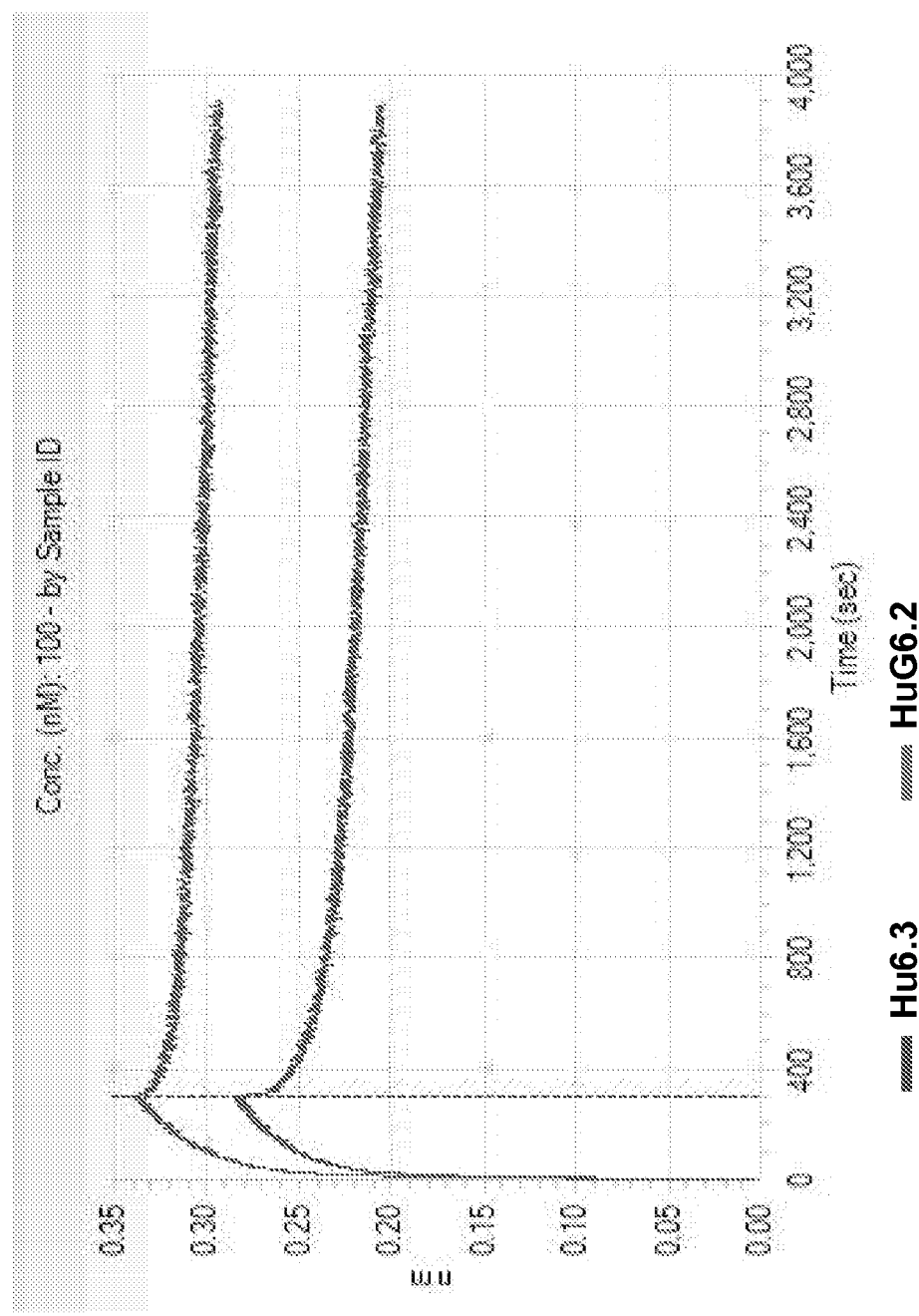
FIG. 7 is a Real time Bio-Layer Interferometry binding analysis of HuG6.2 and HuG6.3 (Thr73Lys mutant) to the biotinylated D80 scFv-Fc.
Figure 8:
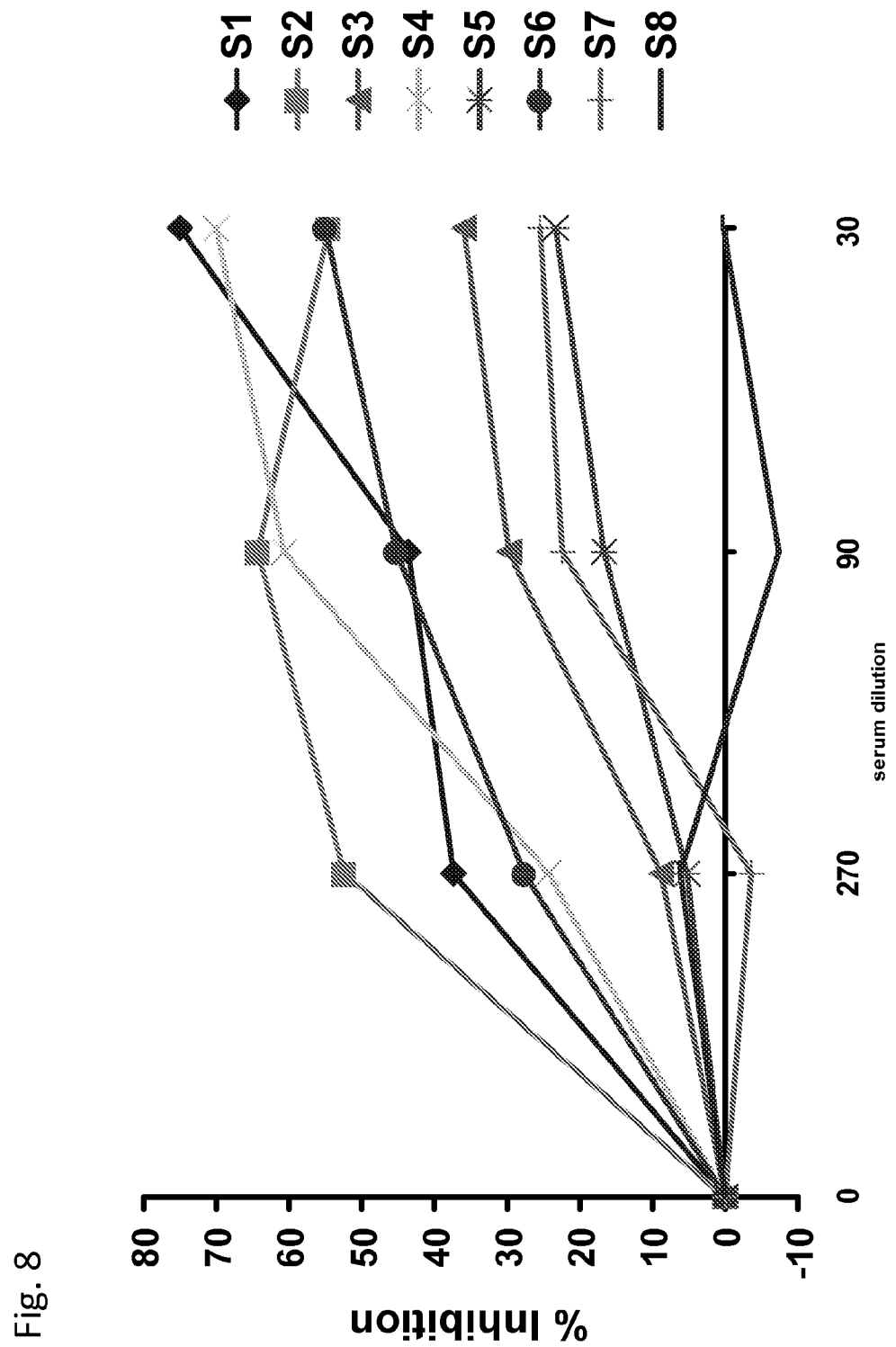
FIG. 8 shows binding of endogenous anti-H5 antibodies to H5 by competition ELISA. 3 ng of purified biotinylated-F10 (Bio-F10) antibodies were mixed with each serum sample at various dilutions and added to H5 (H5-VN04)-coated plates, washed, and followed by HRP-streptavidin incubation to detect biotinylated-F10 bound to H5. Most of serum samples, except No. 8, show ability to inhibit binding of Bio-F10 to H5, indicating the presence of endogenous anti-H5 antibodies in serum samples from healthy individuals.
Figure 9:
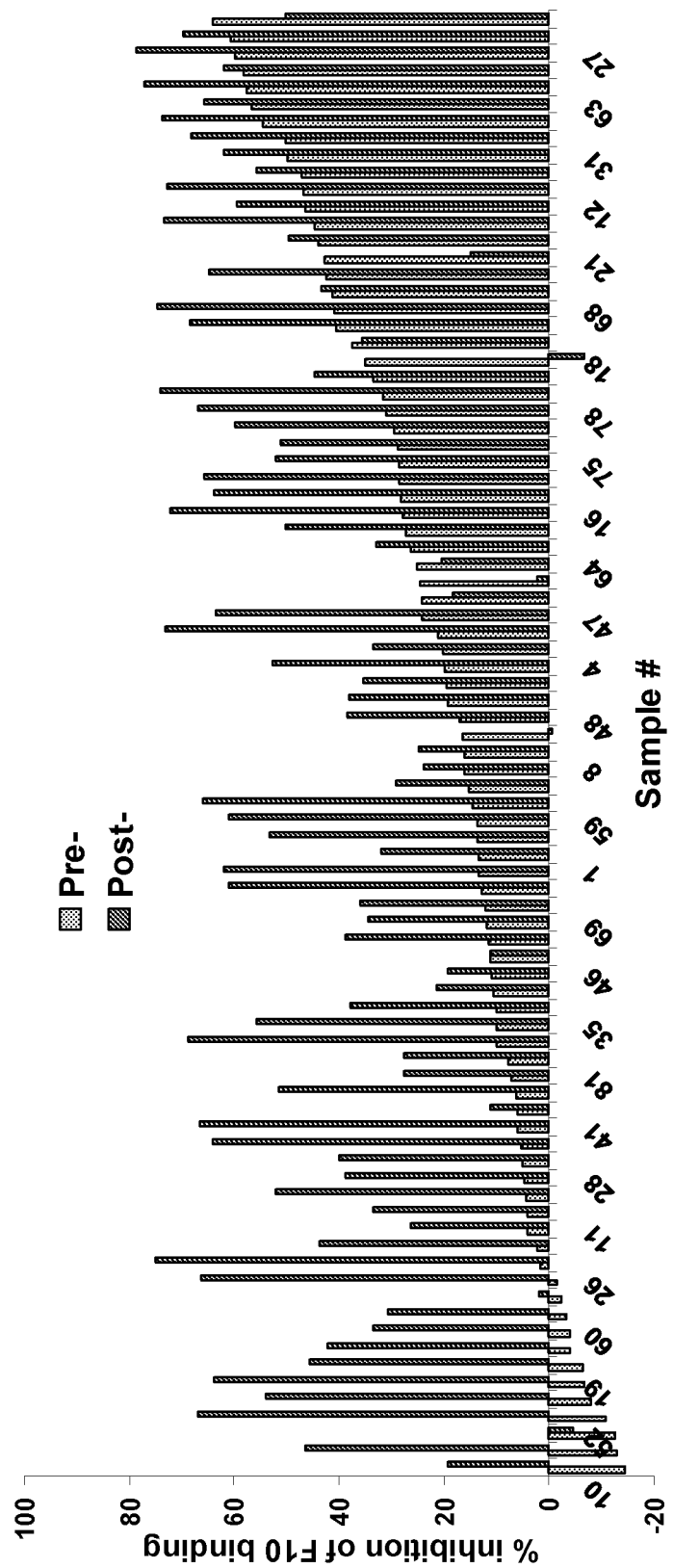
FIG. 9 shows binding of endogenous anti-H5 antibodies to H5 by competition ELISA. Purified biotinylated-F10 (Bio-F10) antibodies were mixed with serum samples obtained before or after H5N1 vaccination from healthy individuals. The mixture was added to H5 (H5-VN04)-coated plates, washed, and followed by HRP-streptavidin incubation to detect biotinylated-F10 bound to H5. Most of pre-vaccinated serum samples show ability to inhibit binding of Bio-F10 to H5, indicating the presence of endogenous anti-H5 antibodies in healthy individuals. H5N1 vaccination boosts the production of anti-H5 antibodies in all of the individuals. The boosting effect is stronger in the individuals with lower amount of endogenous anti-H5 antibodies.
Figure 10:
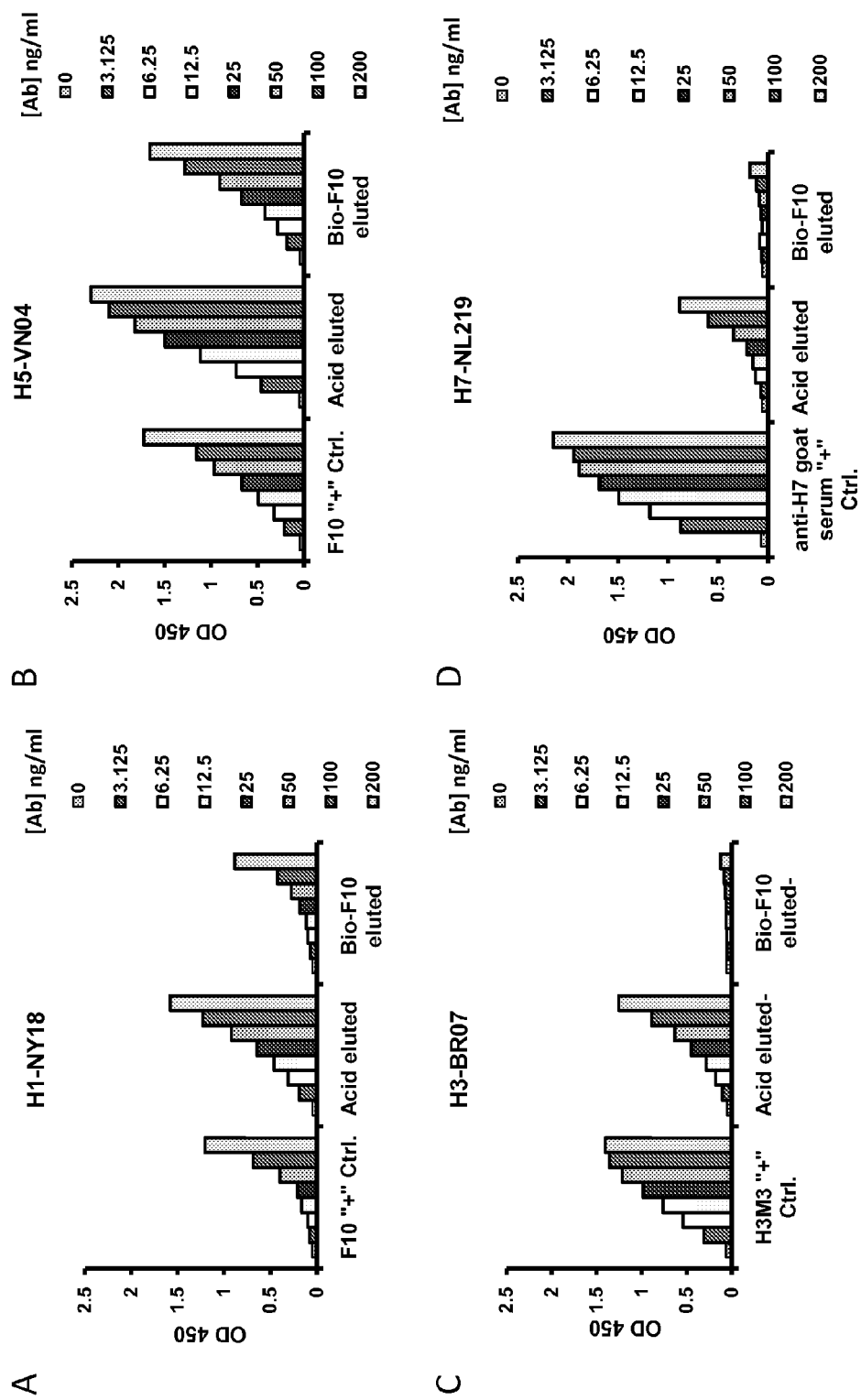
FIG. 10 shows in vitro binding of acid-eluted and biotinylated-F10 (Bio-F10)-eluted anti-H5 fractions from intravenous immunoglobulin (IVIG) samples. Purified F10 antibodies, acid-eluted, and biotinylated-F10 (Bio-F10)-eluted anti-H5 fractions at various concentrations were evaluated for binding to various HA coated on an ELISA plate. (A) Both acid-eluted and Bio-F10-eluted fractions recognize H1-NY18 as control F10 antibodies do. (B) Both acid-eluted and Bio-F10-eluted fractions recognize H5-VN04 as control F10 antibodies do. (C) Only control H3M3 and acid-eluted fraction recognize H3-BR07, but not Bio-F10-eluted fraction. (D) Unlike the control antibody anti-H7, acid-eluted fraction only binds to H7-NL219 at high concentration, and Bio-F10-eluted fraction does not recognize H7-NL219.
Figure 11:
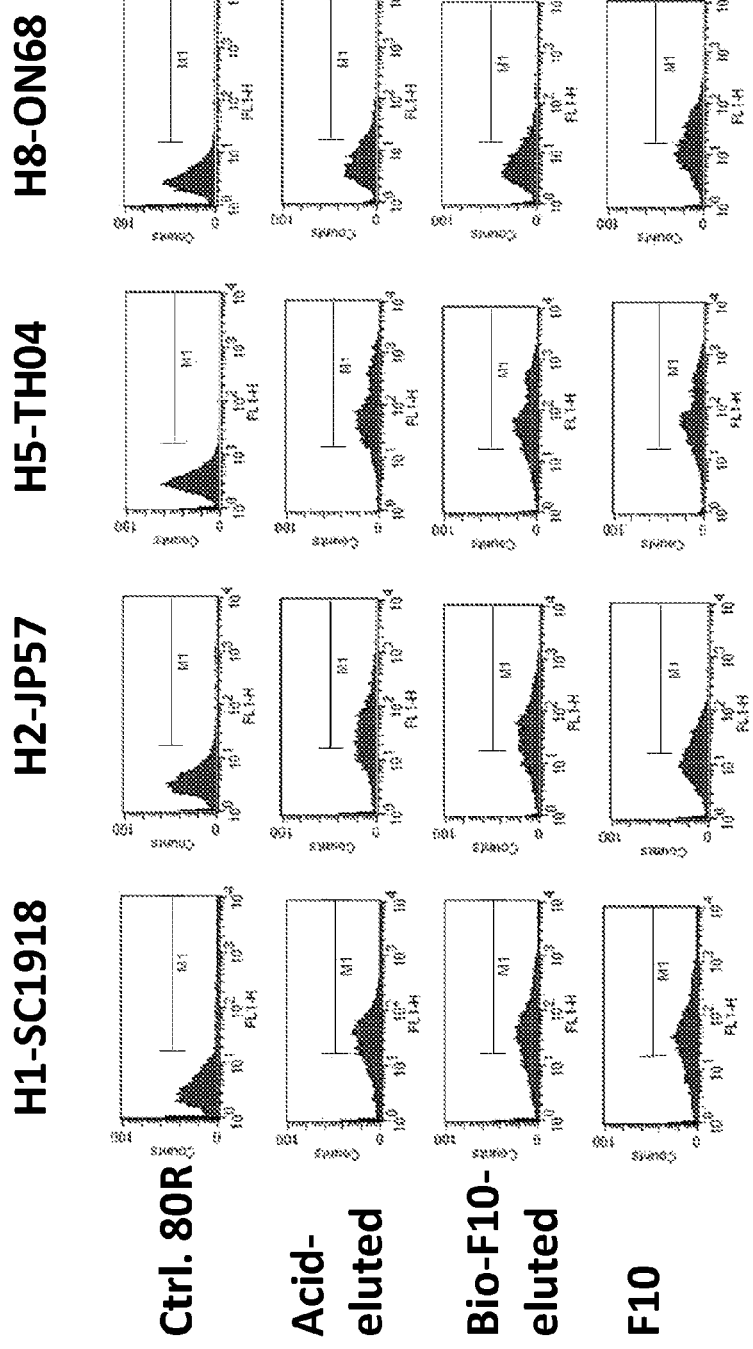
FIG. 11 shows FACS analysis of various anti-H5 eluate fractions binding to H1, H2, H5 (Cluster H1a); and H8 (Cluster H9). 293T cells were transiently transfected with different HA-expressing plasmids, and antibody binding to the cells was analyzed by FACS. H5-specific antibody 80R is the negative control and F10 antibody with broader specificity is the positive control. Both acid-eluted and Bio-F10 anti-H5 fraction can bind to H1, H2 and H5. They do not show much difference in binding to H1, H2 and H5. Complete viral strain designations are: H1-SC1918 (A/South Carolina/1/1918 (H1N1)); H2-JP57 (A/Japan/305/57 (H2N2)); H5-TH04 (A/Thailand/2-SP-33/2004(H5N1)); H8-ON68 (A/Turkey/Ontario/6118/68).
Figure 12:
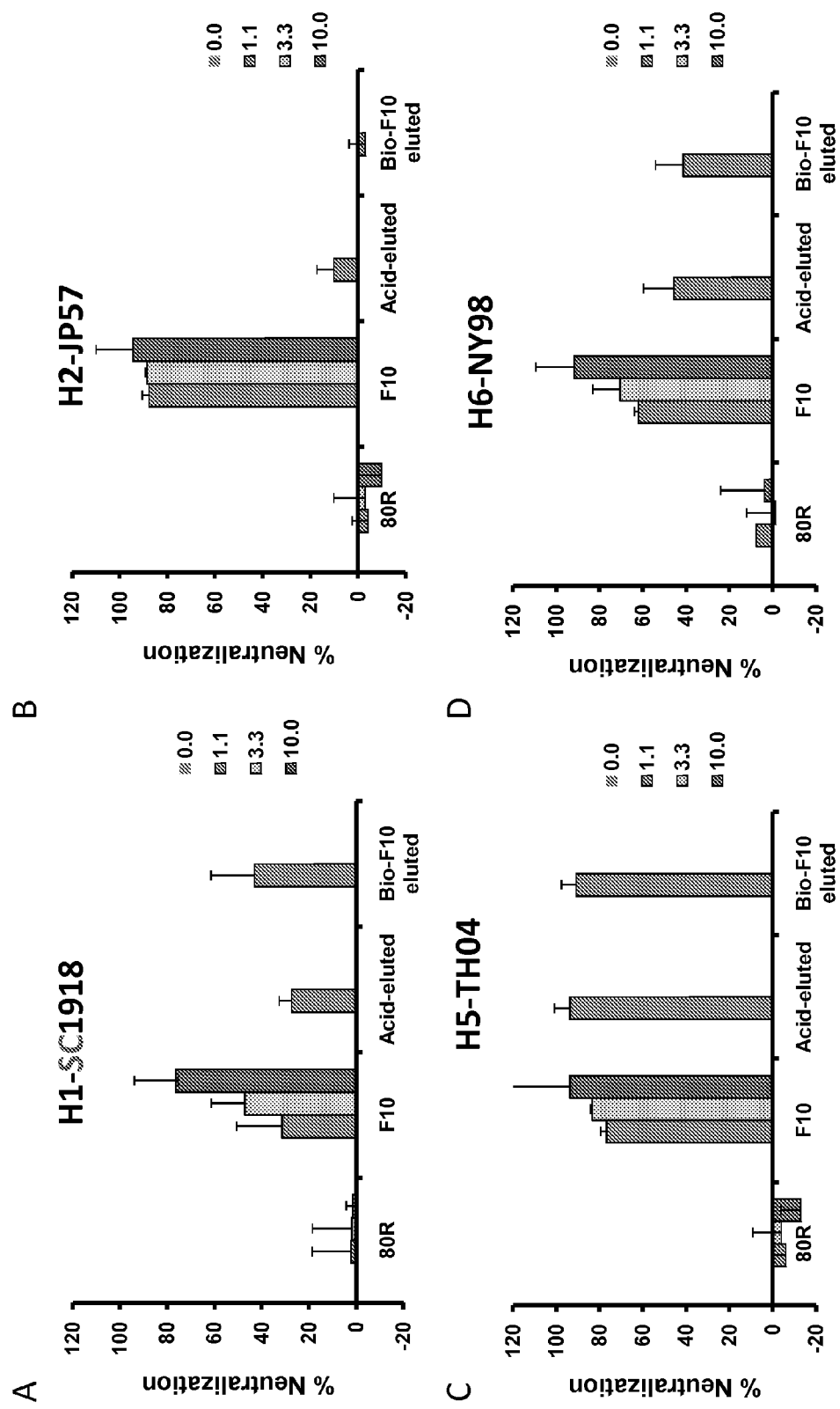
FIG. 12 shows in vitro neutralization of various anti-H5 eluate fractions. Purified F10 antibodies, acid-eluted, and biotinylated-F10 (Bio-F10)-eluted anti-H5 fractions at various concentrations were evaluated for neutralizing activity against individual influenza virus. H5-specific antibody 80R is the negative control and F10 antibody with broader specificity is the positive control. (A) Both acid-eluted and Bio-F10-eluted fractions can neutralize H1-SC1918. (B) Neither acid-eluted nor Bio-F10-eluted fractions can neutralize H2-JP57. (C) Both acid-eluted and Bio-F10-eluted fractions can neutralize H5-TH04. (D) Both acid-eluted and Bio-F10-eluted fractions can neutralize H6-NY98 [H6-NY98 (A/Chicken/New York/14677-13/1998 (H6N2))].
Figure 14:
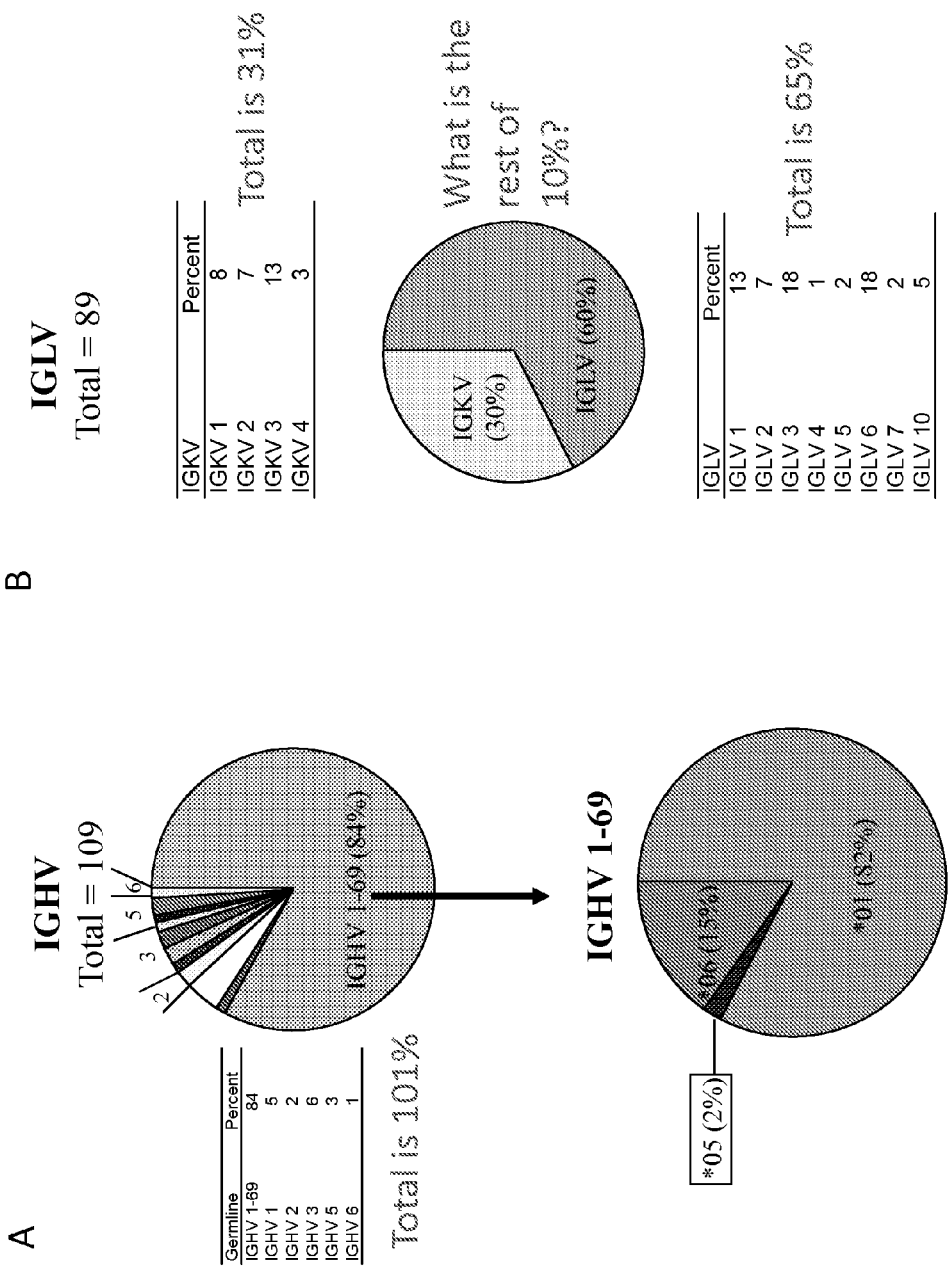
FIG. 14 shows the distribution of antibodies that were isolated by using G6 to pan against the Mehta I/II non-immune library. (A) 84% of the antibodies that bound to G6 were IGHV1-69 and they are primarily comprised of *01 and *05 alleles which encode the critical Phe55 (FIG. 6) that inserts into the hydrophobic pocket on the HA stem (Sui, NSMB '09). This data suggests that this anti-idiotype only recognizes the 51p1 alleles but not the hv1263 alleles. (B) The random assortment of VL chains indicates that the G6 idiotype is only expressed on VH but not VL.
Figure 15:
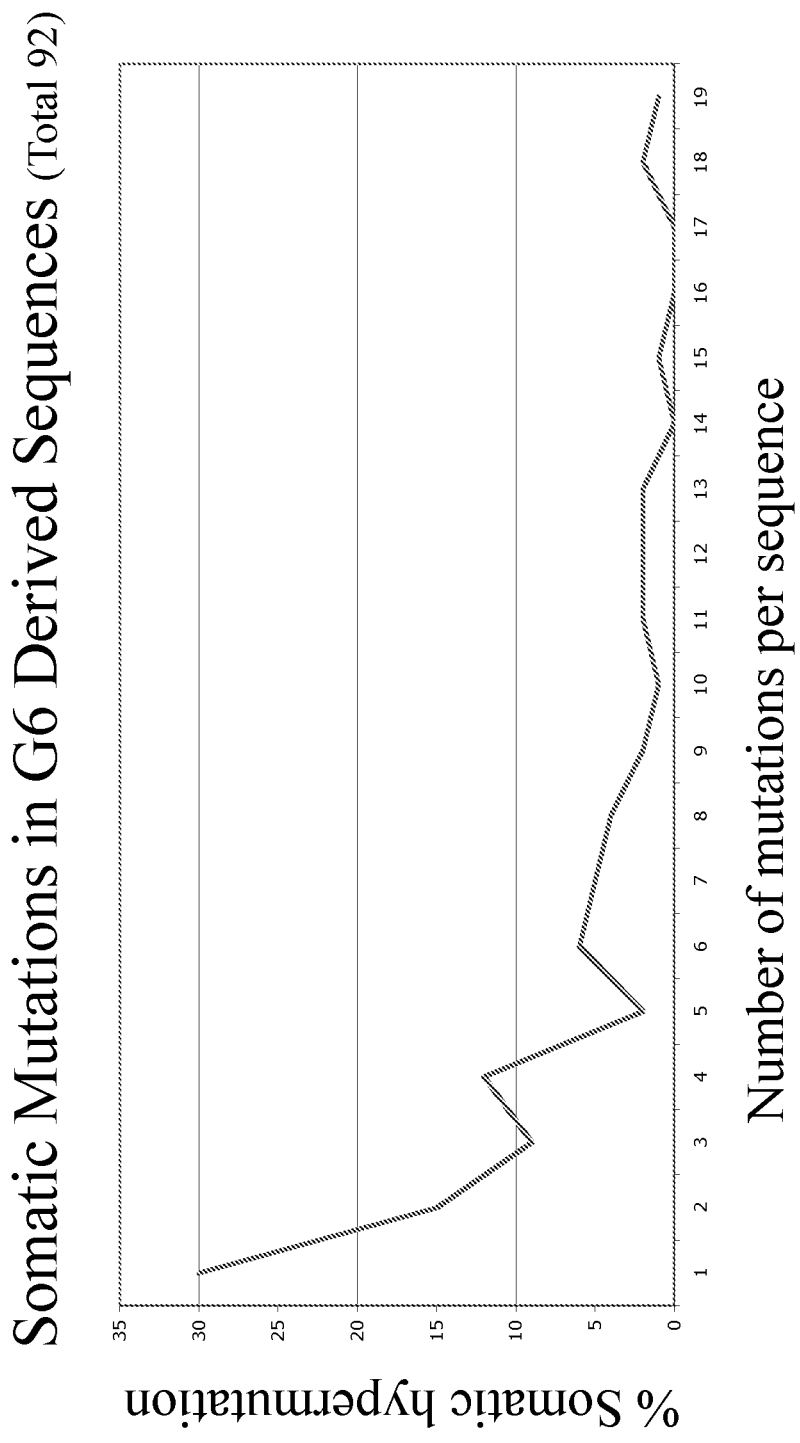
FIG. 15 shows the number of somatic mutations of the VH1-69 encoded antibodies that bound to G6.
Figure 16:
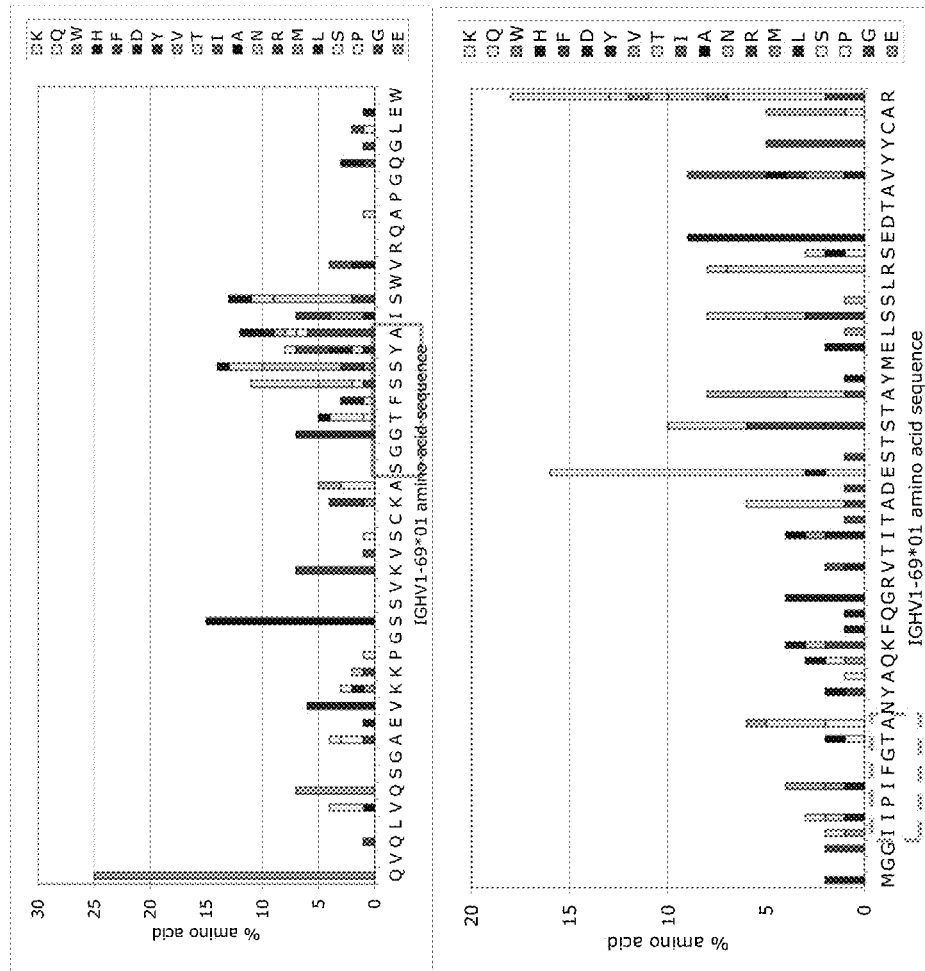
FIG. 16 shows the frequency plot of the different amino acids that were found at each of the positions of the VH1-69 encoded Abs that bound to G6. The frame with solid edges indicates complementarity determining region 1 (CDR1) and the frame with dashed edges indicates CDR2. Note there is much less variability of critical amino acids that are important contact amino acids for HA binding such as the GGT in HCDR1 and Phe55 in CDR2.
Figure 17:
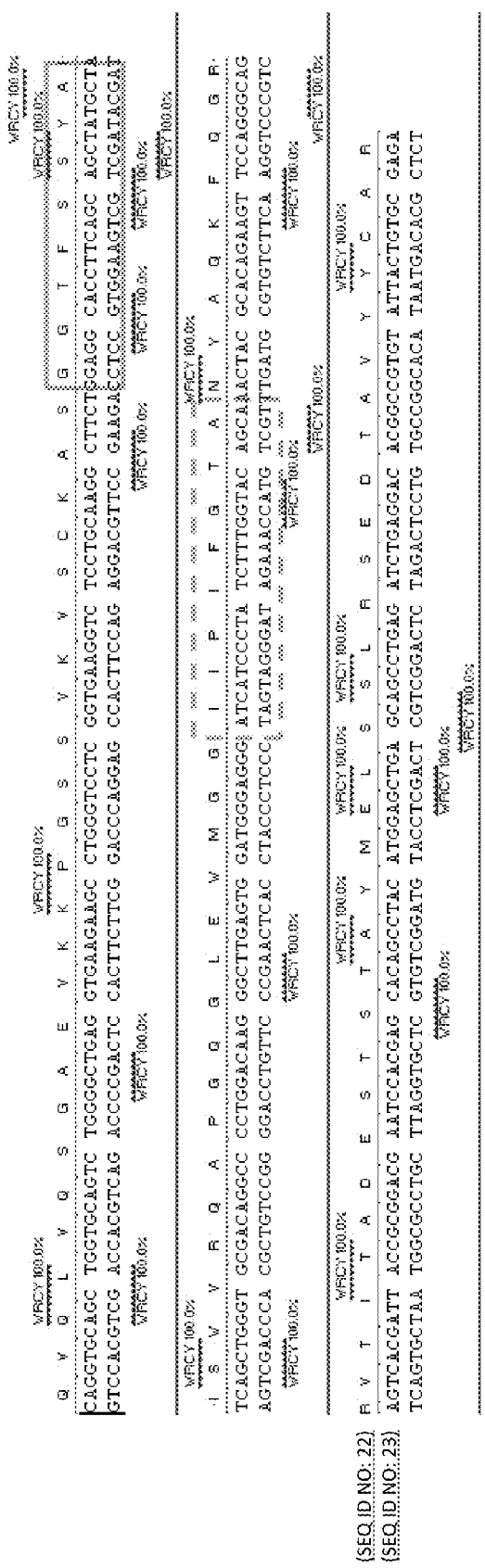
FIG. 17 shows predicated Activation-Induced Deaminase (AID) WRCY motifs on VH1-69. The frame with solid edges indicates complementarity determining region 1 (CDR1) and the frame with dashed edges indicates CDR2. The data shows that there is a paucity of WRCY motifs in the very regions that are needed to mutate that permit rotation of Phe55 to insert into the hydrophobic pocket (shown in the figures below).
Figure 18:
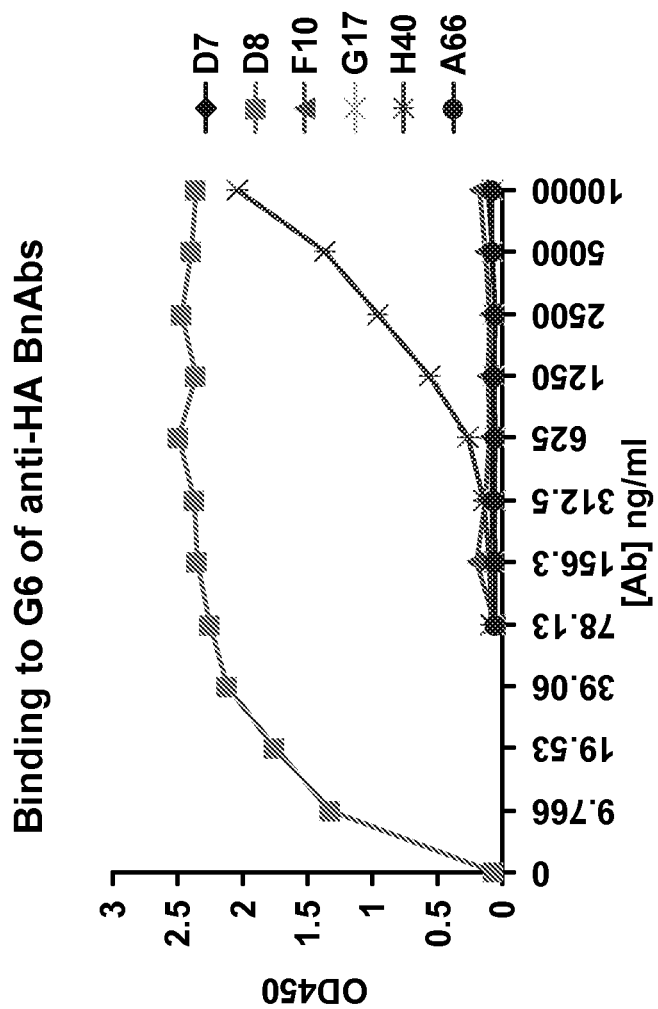
FIG. 18 shows in vitro binding of anti-H5 antibodies. Six anti-H5 BnAbs were evaluated for binding to anti-idiotypic G6 mouse mAb. Only D8 shows positive binding to G6.
Figure 19:
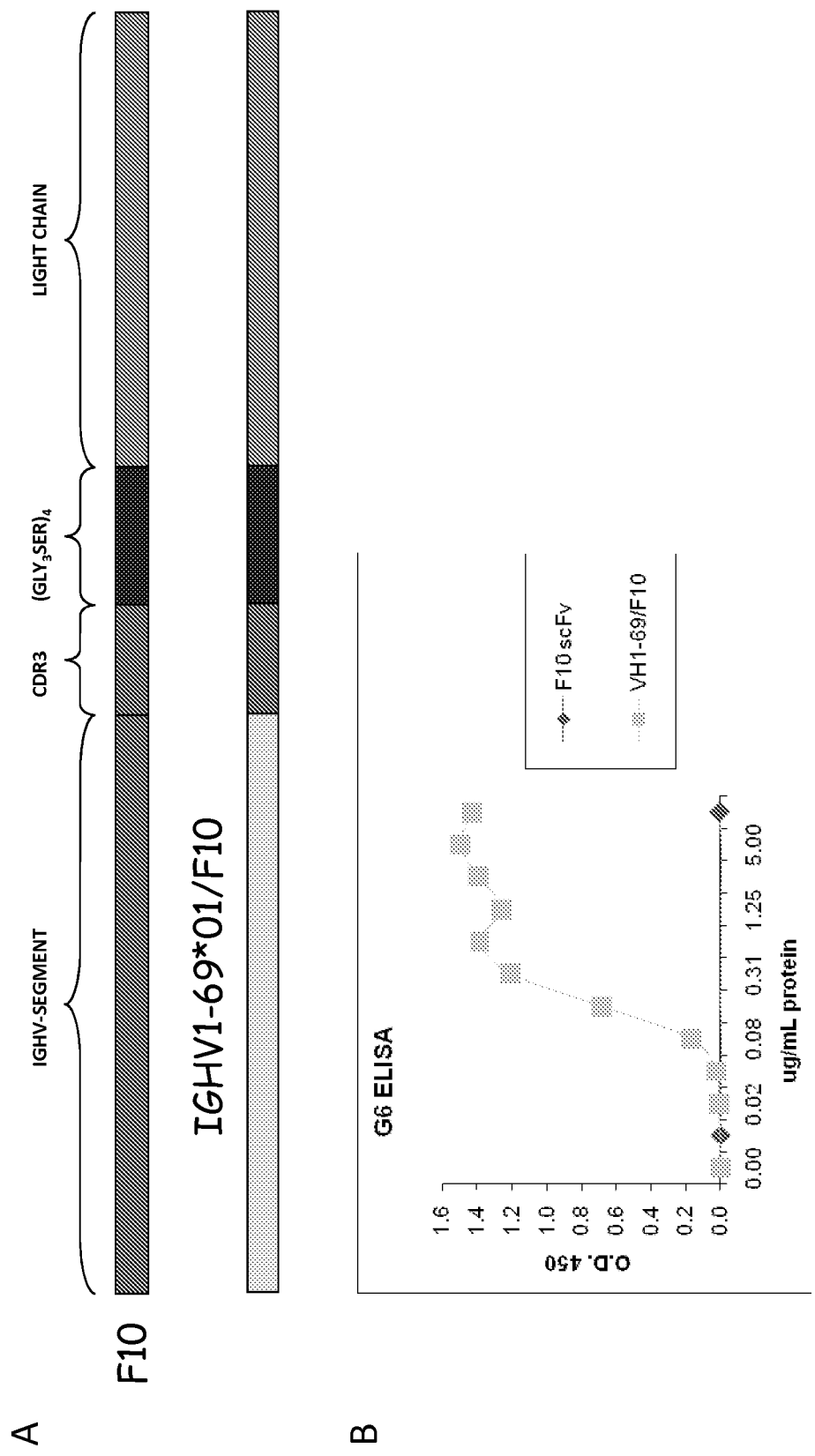
FIG. 19 shows in vitro binding of VH1-69/F10 to G6. (A) The cartoon illustrates the main domains of F10 and the domains of chimeric construct VH1-69/F10. (B) VH1-69/F10 can bind to G6, but F10 cannot. This data confirms that the G6 idiotype is located in the Vh segment.
Figure 20:
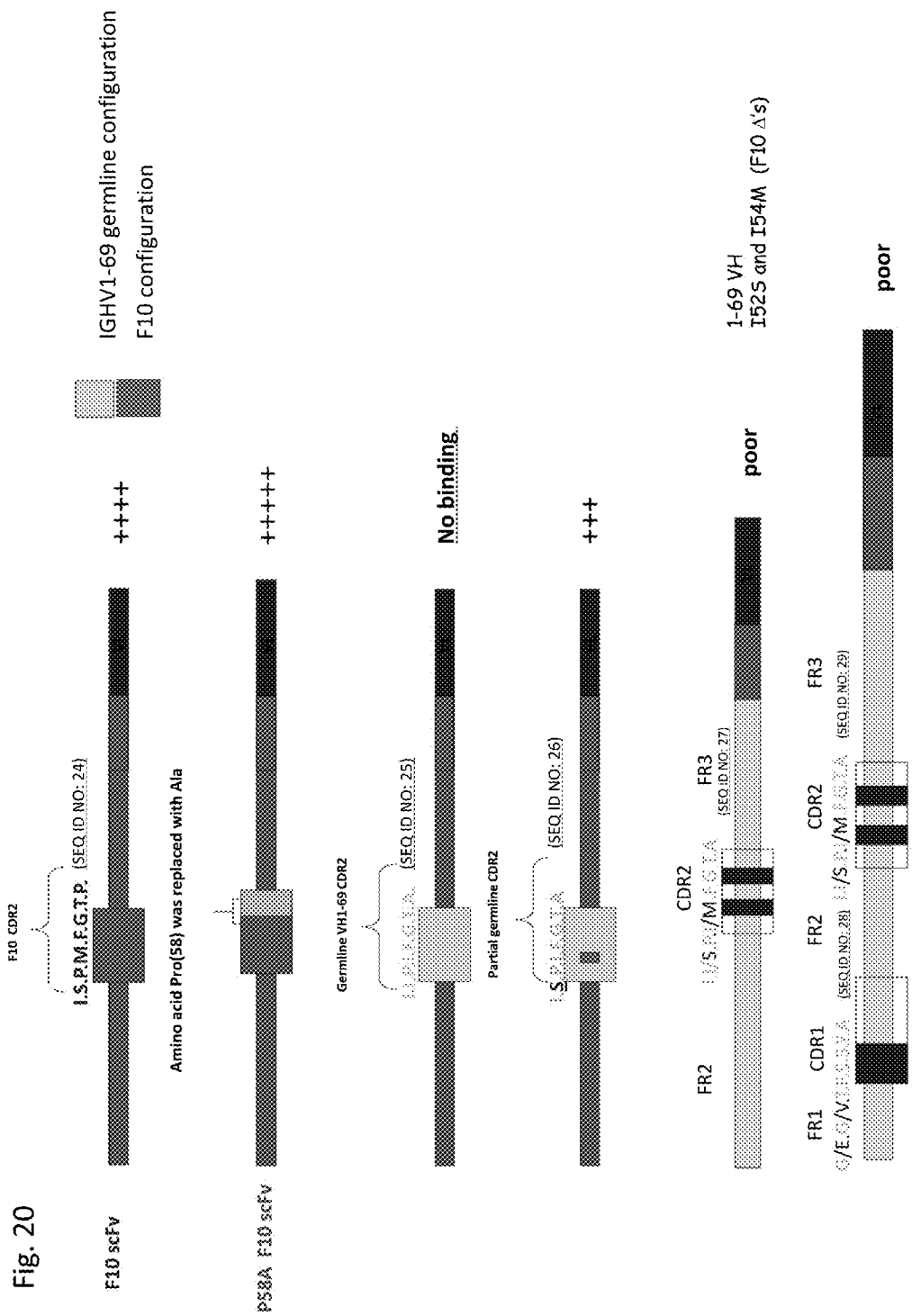
FIG. 20 shows schemes of different chimeric F10 constructs and their binding abilities to H5. Replacement of Pro with Ala outside the binding domain increases binding to H5 (+++++). However, the binding is completely lost when CDR2 is replaced with its germline form. The introduction of Ser back to the sequence recovers 90% of the binding. Replacement of framework regions (FR) with germline form also diminishes the binding. Restoring several key binding residues on the germline background rescues their binding abilities.

The Bio-Layer Interferometry was performed as described above. Briefly the only change was four different concentrations of Human G6.2 and HumanG6.3 scFv-Fcs were used (100 nM, 10 nM, 1 nM and 0 nM). The association and dissociation rates were monitored for 300 secs and 4000 secs respectively. The results showed that HuG6.3 had faster association rates (on) and slower dissociation rates (off) as compared to Human G6.2 as shown in FIG. 7. This suggested that residue $Lys^{73}$ in the framework 3 region of the VH of Hu6.3 is important in binding to D80.

In summary, we have made humanized G6.2 and G6.3 that have similar or better binding activity/kinetics as compared to mouse G6. The estimated affinity for them is within range of 100 pM-1 nM.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1 Whitelegg, N. R. & Rees, A. R. WAM: an improved algorithm for modelling antibodies on the WEB. *Protein Eng* 13, 819-824 (2000).

2 Bruccoleri, R. E. & Karplus, M. Prediction of the folding of short polypeptide segments by uniform conformational sampling. *Biopolymers* 26, 137-168, doi:10.1002/bip.360260114 (1987).

3 Dauber-Osguthorpe, P. et al. Structure and energetics of ligand binding to proteins: *Escherichia coli* dihydrofolate reductase-trimethoprim, a drug-receptor system. *Proteins* 4, 31-47 (1988).

4 Guex, N. & Peitsch, M. C. SWISS-MODEL and the Swiss-PdbViewer: an environment for comparative protein modeling. *Electrophoresis* 18, 2714-2723, doi: 10.1002/elps.1150181505 (1997).

5 Guex, N., Peitsch, M. C. & Schwede, T. Automated comparative protein structure modeling with SWISS-MODEL and Swiss-PdbViewer: a historical perspective. Electrophoresis 30 Suppl 1, S162-173, (2009).

6 Daura, X., Oliva, B., Querol, E., Aviles, F. X. & Tapia, O. On the sensitivity of MD trajectories to changes in water-protein interaction parameters: the potato carboxypeptidase inhibitor in water as a test case for the GROMOS force field. *Proteins* 25, 89-103 (1996).

What is claimed is:

1. An isolated humanized monoclonal antibody, wherein said antibody has
   a humanized heavy chain with three CDRs comprising an amino acid sequence of SEQ ID NO: 5 (GYTFTSYW); SEQ ID NO: 6 (VSPGNSDT); and SEQ ID NO: 7 (TRSRYGNNALDY); and a humanized light chain with three CDRs comprising an amino acid sequence of QGISSNIVW SEQ ID NO: 8 (QGISSNIVW); SEQ ID NO: 9 (HGT); and SEQ ID NO: 10 (VQYSQFPPT),
   wherein said antibody binds human immunoglobulin heavy chain variable region protein encoded by germline gene VH1-69.

2. A composition comprising an isolated humanized monoclonal antibody, wherein said antibody has
   a humanized heavy chain with three CDRs comprising an amino acid sequence of SEQ ID NO: 5 (GYTFTSYW); SEQ ID NO: 6 (VSPGNSDT); and SEQ ID NO: 7 (TRSRYGNNALDY); and a humanized light chain with three CDRs comprising an amino acid sequence of QGISSNIVW SEQ ID NO: 8 (QGISSNIVW); SEQ ID NO: 9 (HGT); and SEQ ID NO: 10 (VQYSQFPPT);
   wherein said antibody binds human immunoglobulin heavy chain variable region protein encoded by germline gene VH1-69;
   the composition further comprising an antigen; and
   wherein said antigen comprises the stem region of the hemagglutinin (HA) protein of an influenza virus.

3. The composition of claim 2, wherein the antibody is a single chain antibody.

4. The composition of claim 2, wherein the antigen is covalently linked to said antibody.

* * * * *